US005573752A

United States Patent [19]
Ranganathan et al.

[11] Patent Number: 5,573,752
[45] Date of Patent: Nov. 12, 1996

[54] AROMATIC AMIDE COMPOUNDS AND METAL CHELATES THEREOF

[75] Inventors: Ramachandran S. Ranganathan, Princeton; Edmund R. Marinelli, Lawrenceville; Radhakrishna Pillai, Kendall Park; Michael F. Tweedle, Princeton, all of N.J.

[73] Assignee: Bracco International B.V., Amsterdam

[21] Appl. No.: 585,290

[22] Filed: Jan. 11, 1996

Related U.S. Application Data

[63] Continuation of Ser. No. 225,210, Apr. 8, 1994, abandoned.
[51] Int. Cl.$^6$ .................................................. A61B 5/055
[52] U.S. Cl. ........................ 424/9.363; 540/465; 540/474; 514/184; 514/836; 436/173; 436/806; 534/15; 534/16
[58] Field of Search ........................ 424/9.363; 540/465, 540/474; 514/184, 836; 128/653.4, 654; 436/173, 806; 534/16, 15

[56] References Cited

U.S. PATENT DOCUMENTS

| | | | |
|---|---|---|---|
| 4,631,337 | 12/1986 | Tomalia et al. | 528/391 |
| 4,647,447 | 3/1987 | Gries et al. | 424/9 |
| 4,687,659 | 8/1987 | Quay | 424/9 |
| 4,859,451 | 8/1989 | Quay et al. | 424/9 |
| 4,885,363 | 12/1989 | Tweedle et al. | 540/46 S |
| 4,899,755 | 2/1990 | Lauffer et al. | 128/654 |
| 4,957,939 | 9/1990 | Gries et al. | 424/9 |
| 4,963,344 | 10/1990 | Gries et al. | 424/9 |
| 4,983,376 | 1/1991 | Sherry | 424/9 |
| 5,021,236 | 6/1991 | Gries et al. | 424/9 |

FOREIGN PATENT DOCUMENTS

| | | |
|---|---|---|
| 78995/87 | 3/1988 | Australia. |
| 31485/89 | 9/1989 | Australia. |
| 61073/90 | 2/1991 | Australia. |
| 2039846 | 10/1991 | Canada. |
| 2 07 867 | 2/1993 | Canada. |
| 0230893 | 8/1987 | European Pat. Off.. |
| 0325762 | 8/1989 | European Pat. Off.. |
| 450742 | 10/1991 | European Pat. Off.. |
| 466200 | 1/1992 | European Pat. Off.. |
| 0 565 930 | 10/1993 | European Pat. Off.. |
| 227421 | 10/1990 | New Zealand. |
| WO89/05802 | 6/1989 | WIPO. |
| WO92/04336 | 3/1992 | WIPO. |

OTHER PUBLICATIONS

Journal of the Chemical Society. Chemical, No. 13, 7 Jul. 1993, Marcella Murru et al., pp. 116–118.

Villringer et al., "Dynamic Imaging with Lanthanide Chelates in Normal Brain: Contrast Due to Magnetic Susceptibilty Effects", Magnetic Resonance in Medicine, 6, 164–174 (1988).

Shehadi, "Contrast Media Adverse Reactions: Occurrence, Recurrence, and Distribution Patterns", Diagnostic Radiology, vol. 143, No. 1, pp. 11–17 (Apr. 1982).

Bettmann, "Angiographic Contrast Agents: Conventional and New Media Compared", AJR, 139, pp. 787–794 (Oct. 1982).

Bettmann et al., "Recent Advances in Contrast Agents", Radiologic Clinics of North America, vol. 24, No. 3, pp. 347–357 (Sep. 1986).

Wedeking et al., "Comparison of the Biodistribution of $^{153}$Gd–Labeled Gd(DTPA)$^{2-}$, Gd(DOTA)$^-$ and Gd(Acetate)$_n$ in Mice", Nucl. Med. Biol., vol. 5, No. 4, pp. 395–402 (1988).

Tweedle et al., "Reaction of Gadolinium Chelates with Endogenously Available Ions", Magnetic Resonance Imaging, vol. 9, pp. 409–415(1991).

Tweedle, "Work in Progress Toward Nonionic Macrocyclic Gadolinium(III) Complexes", in Contrast and Contrast Agents in Magnetic Resonance Imaging, edited by P. A. Rink, European Workshop on Magnetic Resonance in Medicine, pp. 65–73 (1989).

Brechbiel et al., "Synthesis of 1–(p–Isothiocyanatobenzyl) Derivatives of DTPA and EDTA. Antibody Labeling and Tumor–Imaging Studies", Inorg. Chem., 25, pp. 2772–2781 (1986).

Hoey et al., "Chemistry of X–ray Contrast Media", Handbook of Experimental Pharmacology, pp. 23–125 (1984).

Wedeking et al., "Biodistribution and Excretion of New Gd–Complexes in Mice", p. 801 and Multi-Tissue Pharmacokinetic Evaluation of MRI Contrast Agents; p. 802, Society of Magnetic Resonance in Medicine, 8th Annual Meeting, The RAI Congrescentrum, Amsterdam, The Netherlands (Aug. 12–18, 1989).

Cavagna et al., "Biliary Agents: New Formulations", International Symposium & Course, Liver Imaging–Present and Future in MRI, CT & US, Harvard Medical School–Boston, Massachusetts, 3 pages (Jun. 25–27, 1990).

(List continued on next page.)

*Primary Examiner*—Gary E. Hollinden
*Attorney, Agent, or Firm*—George P. Hoare; Donald L. Rhoads

[57] ABSTRACT

Novel aromatic amide compounds comprising a ligand nucleus containing at least one aminocarboxylate, aminophosphonate and/or aminohydroxamate chelating group, substituted with a substituted aromatic amide group of the formula

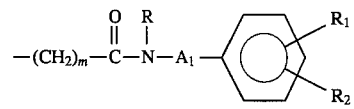

wherein R is

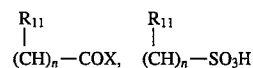

or —[(CH$_2$)$_2$—Y]—R$_{13}$, salts and/or multimers thereof, and metal chelates, particularly useful for MRI of the hepatobiliary system.

16 Claims, No Drawings

OTHER PUBLICATIONS

Broan et al., "Structure and solution stability of indium and gallium complexes of 1,4,7-triazacyclononanetriacetate and yttrium complexes of 1,4,7,10-tetraazacyclododecanetetracetate and related ligands. . . ", J. Chem. Soc., Perkin Trans. 2, No. 1, pp. 87–99 (1991).

Dischino et al., "Synthesis of Nonionic Gadolinium Chelates Useful as Contrast Agents for Magnetic Resonance Imaging. . . ", Inorganic Chemistry, vol. 30, No. 6, p. 1265–1269 (1991).

Tazaki et al., Chem. Abstracts, 1992, CA 97:6274S.

Broan et al., "Synthesis of New Macrocyclic Amino–Phosphinic Acid Complexing Agents and Their C— and P–Functionalised Derivatives for Protein Linkage," Synthesis, pp. 63–68 (1992).

AROMATIC AMIDE COMPOUNDS AND METAL CHELATES THEREOF

This application is a continuation of Ser. No. 08/225,210 filed Apr. 8, 1994, now abandoned.

In accordance with the present invention, novel aromatic amide compounds are provided. The present compounds (also referred to herein as "ligands") comprise a ligand nucleus containing at least one aminocarboxylate, aminophosphonate and/or aminohydroxamate chelating group, substituted with a substituted aromatic amide group, and are represented by the following formula I:

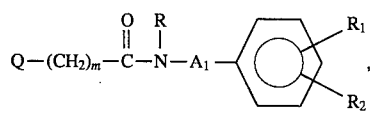

wherein

Q is a ligand nucleus containing at least one aminocarboxylate, aminophosphonate and/or aminohydroxamate chelating group;

$A_1$ is $(CH_2)_m{}'$, $(CH_2)_n$—O—$(CH_2)_n{}'$ or a single bond;

$(CH_2)_m$ and $(CH_2)_m{}'$ may be independently substituted with alkyl or hydroxyalkyl;

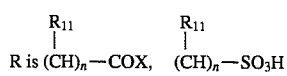

or —[$(CH_2)_2$—Y]—$R_{13}$;

X is —OH, —O-alkyl or —$NHR_{12}$;

Y is —O— or —NH—;

$R_1$ and $R_2$ are each independently hydrogen, alkyl, cycloalkyl, aryl, arylalkyl, —$NO_2$, —$NH_2$,

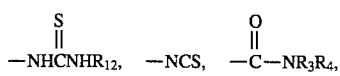

—COOH, —N—N$^+$≡N$^-$, —$NR_3COR_9$, haloalkyl, $C_{1-8}$ alkoxy, aryloxy, cycloalkyloxy, or a functional group capable of forming a conjugate with a biomolecule or of forming a multimer of said compound of the formula I, or $R_1$ and $R_2$ together with the phenyl ring to which they are bonded form a naphthyl group (especially 1- or 2-naphthyl), with the proviso that at least one of $R_1$ or $R_2$ must be other than hydrogen;

$R_3$ and $R_4$ are independently hydrogen, alkyl, arylalkyl, aryl, alkoxy or hydroxyalkyl, or $R_3$ and $R_4$, together with the nitrogen atom to which they are bonded, form a maleimide group;

$R_9$ is alkyl or hydroxyalkyl;

each $R_{11}$ is independently hydrogen or alkyl;

$R_{13}$ is —$CH_2COOH$ or —$CH_2CONHR_{12}$;

$R_{12}$ is hydrogen, alkyl, —$NH_2$,

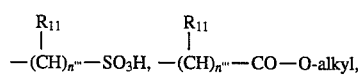

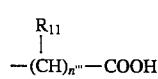

or hydroxyalkyl;

m, m', n, n' and n''' are independently 1 to 5;

and salts and/or multimeric forms thereof.

It is understood herein that, while it is not necessary that those groups recited above as $R_1$ or $R_2$ substituents be functional groups, one or more of the $R_1$ or $R_2$ groups recited prior to the term "functional group capable of forming a conjugate with a biomolecule or of forming a multimer of said compound of the formula I," such as —NCS, may also be capable of forming a conjugate with a biomolecule or a multimer.

The present compounds are useful, for example, as metal-chelating ligands, and, in the form of metal complexes, are especially useful as diagnostic contrast agents. When the metal is paramagnetic, such agents are suitable for magnetic resonance imaging, and are particularly useful for magnetic resonance imaging (MRI) of the liver and biliary tree (bile ducts).

The present invention thus also provides the novel metal complexes formed by complexing a compound of the present invention with a metal, as well as the use of these metal complexes in diagnostic imaging. It is preferred that the present ligands be amphiphilic, that is, partition to at least some extent between both lipophilic and hydrophilic liquid phases, especially where use as hepatobiliary agents is contemplated.

DETAILED DESCRIPTION OF THE INVENTION

The term "ligand nucleus containing at least one aminocarboxylate, aminophosphonate and/or aminohydroxamate chelating group", as used throughout this specification, refers to moieties which contain at least two chelating groups and which are capable of chelating a metal, wherein at least one of said chelating groups is an aminocarboxylate chelating group, an aminophosphonate chelating group or an aminohydroxamate chelating group.

The terms "aminocarboxylate chelating group", "aminophosphonate chelating group" and "aminohydroxamate chelating group", as used throughout this specification, refer to groups containing a nitrogen atom bonded through a methylene (—$CH_2$—) or ethylene (—$CH_2$—$CH_2$—) group to a carboxylate (—$COOY_1$), phosphonate (—$PO_3HY_1$) or hydroxamate (—$CONHOY_1$) group, respectively, wherein said methylene or ethylene group may optionally be substituted, such as with alkyl, hydroxyalkyl or aralkyl. As used herein, $Y_1$ is a hydrogen atom, or a cation, preferably a physiologically biocompatible cation of an inorganic or organic base or amino acid.

Any ligand nucleus having the above characteristics may suitably be employed, such as those known in the field of diagnostic contrast agents, or those contained in the compounds I', I'', I''' or I'''' described further below. Particularly preferred such nuclei include those containing three or more chelating groups, most preferably the nucleus of the compound I' described below.

The term "alkyl", as used throughout this specification, refers to both straight and branched chain groups having 1 to 21 carbon atoms. Alkyl groups having 1 to 12, and especially 1 to 5, carbon atoms are preferred. The term "haloalkyl", as used throughout this specification, refers to an alkyl group substituted by one or more halogen atoms, such as trifluoromethyl. The term "alkoxy", as used throughout this specification, refers to an alkyl group as described above bonded through an oxygen linkage (—O—).

The term "aryl", as used throughout this specification, refers to phenyl and substituted phenyl. Preferred substituted phenyl groups are those substituted with 1, 2 or 3 halo, hydroxyl, hydroxyalkyl, alkyl, aryl, alkoxy, carbamoyl (—CONH$_2$), carboxamide (—NHCOOY$_1$), acylamino (—NH-acyl) or carboxyl (—COOY$_1$) moieties. The term "aryloxy", as used throughout this specification, refers to an aryl group as described above bonded through an oxygen linkage.

The term "hydroxyalkyl", as used throughout this specification, refers to straight and branched alkyl groups including one or more hydroxy radicals such as —CH$_2$CH$_2$OH, —CH$_2$CH(OH)CH$_2$OH, —CH(CH$_2$OH)$_2$ and the like. (Sovak, M., editor *Radiocontrast Agents*, Springer-Verlag, 1984, pp. 1–125 describes hydroxyalkyl chemistry).

The terms "arylalkyl" or "aralkyl", as used throughout this specification, refer to an aryl group as described above, bonded through an alkyl group as described above.

The term "cycloalkyl", as used throughout this specification, refers to saturated, cyclic, unsubstituted or substituted, hydrocarbon ring systems, preferably containing 1 to 3 rings and 3 to 7 carbons per ring. Preferred cycloalkyl substituents include aryl groups as described above and/or those groups described above as preferred phenyl substituents. The term "cycloalkyloxy", as used throughout this specification, refers to a cycloalkyl group as described above bonded through an oxygen linkage.

The term "acyl", as used throughout this specification, refers to the moiety formed by removal of the hydroxyl group from the group —COOH of an organic carboxylic acid.

Exemplary compounds of the present invention include those having the formulae $x_1$ is —COOY$_1$, —PO$_3$HY$_1$ or —CONHOY$_1$, where Y$_1$ is as defined above;

R$_{14}$ is hydrogen, alkyl, hydroxyalkyl or aralkyl;

A$_2$ is —CHR$_6$—CHR$_7$—, —CH$_2$CH$_2$(ZCH$_2$—CH$_2$)$_{n''}$—,

—CH$_2$—CH(N(CH$_2$X$_1$)$_2$)—CH$_2$— or —CH$_2$—CH$_2$—N(CH$_2$—CH$_2$—N(CH$_2$X$_1$)$_2$)—CH$_2$—CH$_2$—, wherein X$_1$ is as defined above;

each R$_5$ is independently hydrogen or alkyl (especially methyl);

R$_6$ and R$_7$ together represent a trimethylene group or a tetramethylene group or individually are, independently, hydrogen atoms, lower alkyl groups (e.g., 1–8 carbons), phenyl groups, benzyl groups or R$_6$ is a hydrogen atom and R$_7$ is —(CH$_2$)$_p$—C$_6$H$_4$—W-protein where p is 0 or 1, W is —NH—, —NHCOCH$_2$— or —NHCS—, and protein represents a protein residue (that is, a protein or fragment thereof bonded to W);

n'' is 1, 2 or 3;

Z is an oxygen atom or a sulfur atom or the group NCH$_2$X$_1$ or NCH$_2$CH$_2$OR$_8$ wherein X$_1$ is as defined above and R$_8$ is lower alkyl (e.g., 1–8 carbons);

V is X$_1$ or is —CH$_2$OH, —CONH(CH$_2$)$_r$X$_1$ or —COB, wherein X$_1$ is as defined above, B is a protein or lipid residue (where "protein residue" is a protein or fragment thereof bonded to the carbonyl group of the group —COB and "lipid residue" is a lipid bonded to said carbonyl group), r is an integer from 1 to 12, or if R$_5$, R$_6$ and R$_7$ are each hydrogen, then both V's may together form the group

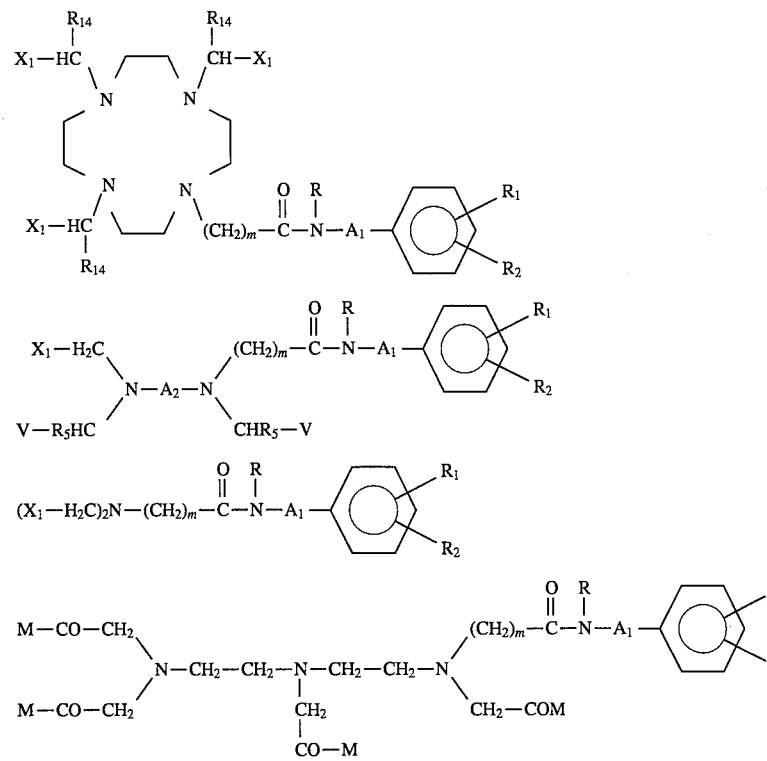

wherein m, R, A$_1$, R$_1$ and R$_2$ are as defined above for formula I and further wherein

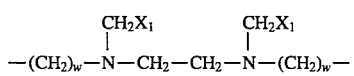

where $X_1$ is as defined above, w is 1, 2 or 3; and each M is independently —OH, —OR$_{10}$, —NH$_2$, —NHR$_{10}$ or NR$_{10}$R$_{10'}$, wherein R$_{10}$ and R$_{10'}$ are independently selected from alkyl groups of up to 18 carbon atoms which may be substituted (for example, by hydroxyalkyl groups), with the proviso that at least one, and preferably 2 or 3 (most preferably 3) M's are —OH. In formula I'''', one M may also be the group

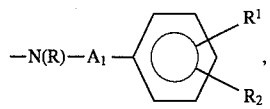

where R, A$_1$, R$_1$ and R$_2$ are as defined above. For metal complex formation, it is preferred that at least two of the substituents Y$_1$ represent metal ion equivalents of an element with an atomic number of 21 to 29, 39 to 50 or 57 to 83.

The compounds of formula I and salts and/or multimers thereof, particularly compounds of the formulae I', I'', I''' and I'''' and salts and/or multimers thereof, may be complexed with paramagnetic metal atoms and used as relaxation enhancement agents for magnetic resonance imaging. These agents, when administered to a mammalian host (e.g., a human) distribute in various concentrations to different tissues, and catalyze relaxation of protons (in the tissues) that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times, generally before and after administration of the agents, and the differences in the images created by the agents' presence in tissues may be used in diagnosis. In proton magnetic resonance imaging, paramagnetic metal atoms such as gadolinium(III), and octahedral manganese(II), chromium(III) and iron(III) (all are paramagnetic metal atoms with a symmetrical electronic configuration) are preferred as metals complexed by the ligands of formula I; gadolinium(III) is most preferred due to the fact that it has the highest paramagnetism, low toxicity, when complexed to a suitable ligand, and high lability of coordinated water.

The metal-chelating ligands of the present invention may be complexed with elements of atomic number 21 to 29, 39 to 50 or 57 to 83, and especially with a lanthanide element (atomic number 58 to 71) and used as chemical shift agents in magnetic resonance imaging or in magnetic resonance in vivo spectroscopy.

Paramagnetic metal complexes of the present invention are particularly useful as hepatobiliary agents, i.e., for magnetic resonance imaging of the liver and biliary tree (bile ducts).

While the above-described uses for the metal-chelating ligands of the present invention are preferred, those working in the diagnostic arts will appreciate that the ligands may also be complexed with the appropriate metals and used as contrast agents in X-ray imaging, radionuclide imaging and ultrasound imaging.

Use in Imaging

To use the ligands of the present invention for imaging, they are preferably first complexed with an appropriate metal. This may be accomplished by methodology known in the art. For example, the metal can be added to a liquid such as water or a water/alcohol mixture in the form of an oxide or in the form of a halide or acetate and treated with an equimolar amount of a ligand of the present invention. The ligand can be added as an aqueous solution or suspension. Dilute acid or base can be added (where appropriate) to maintain a suitable pH. Heating at temperatures as high as 100° C. for periods up to 24 hours or more may sometimes be employed to facilitate complexation, depending on the metal and the chelator, and their concentrations.

Pharmaceutically acceptable salts of the metal complexes of the ligands of this invention are also useful as imaging agents. They may be prepared by using a base (e.g., an alkali metal hydroxide, meglumine, arginine or lysine) to neutralize the above-prepared metal complexes while they are still in solution. Some of the metal complexes are formally uncharged and do not need cations as counterions. Such neutral complexes may be preferred as intravenously administered X-ray and NMR imaging agents over charged complexes because they may provide solutions of greater physiologic tolerance due to their lower osmolality. However, for use as hepatobiliary agents, negatively charged ligands are preferred.

The present invention provides pharmaceutical compositions, comprising a compound of the formula I, or a salt and/or multimer thereof, optionally complexed with a metal, and a pharmaceutically acceptable vehicle or diluent. The present invention further provides a method for diagnostic imaging, comprising the steps of administering to a host a compound of the formula I, or a salt and/or multimer thereof, which is complexed with a metal, and obtaining a diagnostic image, preferably a magnetic resonance image, of said host.

Sterile aqueous solutions of the chelate complexes of the present invention are preferably administered to mammals (e.g., humans) orally, intrathecally and, especially, intravenously in concentrations of 0.003 to 1.0 molar. Use of the metal complexes of the present invention as hepatobiliary agents is preferred; for example, for visualization of the liver, the dose is preferably 0.1 to 0.3 millimole/kilogram. While visualization of the liver and biliary tree is preferred, the metal complexes of the present invention may be employed for visualization of other sites. For example, the present metal complexes may be used for the visualization of brain lesions using magnetic resonance imaging, preferably where a gadolinium complex of a ligand of the formula I is administered intravenously at a dose of 0.05 to 0.5 millimole of the complex per kilogram of mammal body weight, most preferably at a dose of 0.1 to 0.3 millimole/kilogram. For visualization of the kidneys, the dose is preferably 0.05 to 0.25 millimole/kilogram. For visualization of the heart, the dose is preferably 0.25 to 1.0 millimole/kilogram.

The pH of a formulation of the present metal complexes is preferably between about 6.0 and 8.0, most preferably between about 6.5 and 7.5. Physiologically acceptable buffers (e.g., tris(hydroxymethyl)aminomethane) and other physiologically acceptable additives (e.g., stabilizers such as parabens) may be present.

It is also advantageous to employ dual scavenging excipients such as those described in copending application U.S. Ser No. 032,763 filed Mar. 15, 1993 entitled "DUAL FUNCTIONING EXCIPIENT FOR METAL CHELATE CONTRAST AGENTS", incorporated herein by reference. Those excipients have a general formula corresponding to:

wherein D and D' are independently Ca or Zn, L' is an organic ligand which may be different than or the same as the ligand employed to complex the metal and s and t are independently 1, 2 or 3.

Use for Radiotherapy or Imaging Where the Metal-Chelate-Complex is Bound to a Biomolecule Compounds of the present invention include those wherein $R_1$ and/or $R_2$ are functional group(s) capable of forming a conjugate with a biomolecule or of forming a multimer. Any functional groups having at least one of the aforementioned capabilities may be employed. Preferred biomolecules are proteins, particularly monoclonal antibodies or fragments thereof; mono-, oligo- or polysaccharides; mono-, oligo- or polynucleotides or deoxynucleotides (single or double stranded); lipids; or peptides, which may be conjugated to the compounds of the present invention. Conjugates where a compound of the formula I or salt and/or multimer thereof is linked to a biomolecule such as a protein, provided by the present invention, are novel, as are metal complexes and pharmaceutical compositions containing, and methods of using (e.g., for imaging or radiotherapy as described following), the aforementioned conjugates. Conjugation may be achieved in vitro, such as by use of known conjugation methodologies (e.g., those described following), or in situ in a living subject by administration of a compound containing one or more of the aforementioned functional groups.

For protein conjugation, preferred groups $R_1$ and/or $R_2$ include —NH—C(S)—NH—NH$_2$, —COOH,

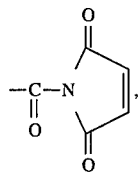

or —N—N$^+$≡N$^-$, or, most preferably, —NCS.

The bifunctional metal-chelating ligands of the present invention may be bound to a monoclonal antibody or a fragment thereof for use in radiotherapy. Monoclonal antibodies are useful in that they can be used to target radionuclides to cancer or tumor sites with great specificity. The compounds of this invention wherein $R_1$ and/or $R_2$ are other than hydrogen, particularly compounds where such groups are the aforementioned preferred groups for protein conjugation, may be linked to monoclonal antibodies or fragments thereof.

Methods for linking the bifunctional chelate to an antibody or antibody fragment include those known in the art, such as those methods described by Brechbiel et al., *Inorganic Chemistry*, 1986, 25, 2772. The method employed may be selected primarily based on the particular bifunctional chelate and secondarily on the antibody or fragment thereof. For example, when the formula I, preferably formula I', compound contains groups where $R_1$=H and $R_2$=—NCS, 10 μL of a 5.0 mM aqueous solution of the formula I chelator may be reacted with 0.5 mL of a 5.0 mg/mL monoclonal antibody (such as B72.3 purchaseable from Damon Biotech Corporation) in 50 mM Hepes buffer at pH 8.5. Aqueous triethylamine (1.5M, 16 μL) may be added. After 2 hours reaction time, the monoclonal antibody may be purified by dialysis. This procedure provides between 1 and 2 formula I chelator molecules bound to each monoclonal antibody. Radioactive metal ion (for example $^{90}$Y) may then be added to the monoclonal antibody-bound chelator by methods such as those known in the art. For example, $^{90}$Y as the $^{90}$Y(III)(acetate)$_3$(H$_2$O)$_4$ (approximate formula in aqueous solution) can be reacted with the monoclonal antibody-bound chelate in solutions where the concentration of each is between $10^{-5}$ and $10^{-7}$ molar and the pH is 6. Dialysis against citrate may then used to purify the product.

An alternative, and preferred method follows that described above, but substitutes the metal-chelate complex for the chelating ligand. To use this method the metal chelate complex is first made by reacting metal-oxide, -halide, -nitrate, -acetate, or the like with formula I chelator. For the chelator described above the acetate of $^{90}$Y at <$10^{-6}$M may be reacted with the chelator at about $10^{-3}$M at pH 6, the chelate complex purified by ion exchange or reverse phase HPLC chromatography, and the metal complex then reacted with the monoclonal antibody as described above for the chelator. The bifunctional, metal-containing, linked antibody, such as in the form of an aqueous solution of the $^{90}$Y-formula I chelator-monoclonal antibody compound, may, for example, be injected intravenously, subcutaneously, intraparentoneally or intralymphatically into a human or other animal with a tumor to which the monoclonal antibody is specific. This allows the radioactive metal ion to be directed to the tumor for which it is intended. The intravenous dosage used is preferably 0.1 to 0.4 millicurie per kilogram of body weight.

Preferred embodiments for when the compounds of the present invention are linked to a protein are those where the $R_1$ and/or $R_2$ groups are —NCS and these group(s) are reacted with a protein to produce a protein conjugate. Preferred proteins are those in serum, wherein the $R_1$ and/or $R_2$=—NCS compound is directly injected and the conjugate is formed in situ. It is understood that other functional groups, as described above, may be used to link the bifunctional metal-chelating ligands of this invention to proteins such as monoclonal antibodies or fragments thereof; mono-, oligo- or polysaccharides; mono-, oligo-, or polynucleotides or deoxynucleotides (single or double stranded); lipids; or peptides.

The present invention also includes multimeric forms of the compounds of formula I or salts thereof, i.e., two or more compounds of the formula I linked together by any suitable linking moiety, such as dimers, trimers, tetramers, etc. Functional groups and technology such as those discussed above regarding conjugation with biomolecules are readily useable to provide such multimers. The functional groups provided onto the phenyl ring

can be, for example, $R_2$=—NCS, activated carboxy functionalities, maleimides and the like, especially where $R_2$ is —NH—C(S)—NHR$_{12}$ and $R_{12}$ is methyl or ethyl. Thus, exemplary multimers of formula I are shown by

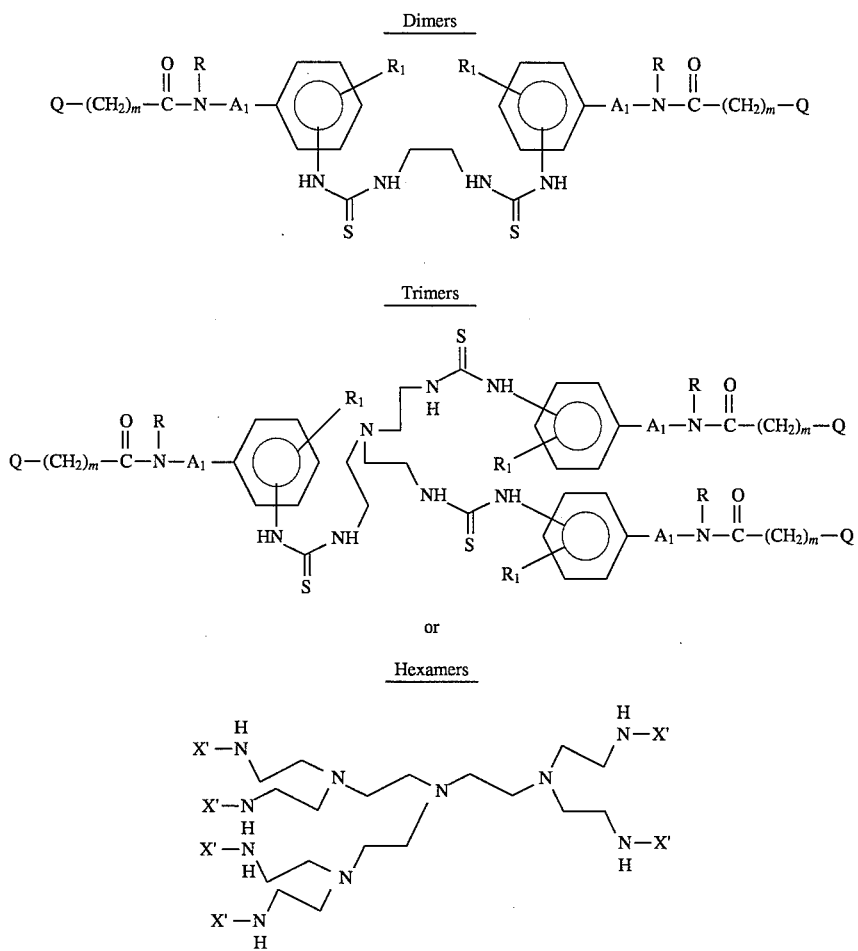

where X' is

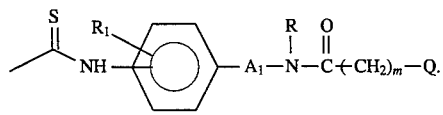

In addition to being formed by linking compounds of the formula I through the $R_1$ and/or $R_2$ groups thereof, multimers may also be formed by linking compounds of the formula I through the R groups thereof. Thus, for example, dimers of compounds of the formula I where R is

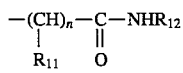

may be formed through an ethylenic linkage wherein the dimers have the following structure:

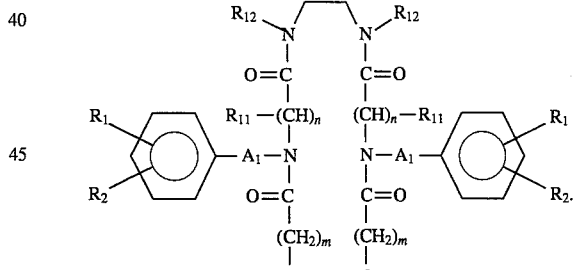

Such compounds may be formed by methods analogous to those described in the Schemes below for the formation of compounds of the formula I. For example, for compounds where $R_{12}$ is

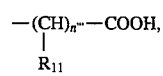

ethylenediamine may be reacted, in a solvent such as dimethylformamide, with the compound

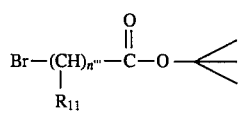

XXIX to form the compound

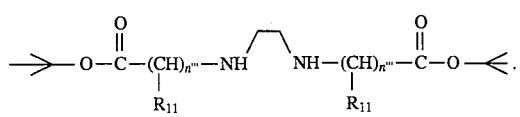   XXX

The compound XXX may be converted to the following compound:

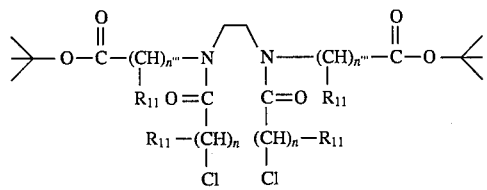   XXXI by contact with a chloroacyl compound

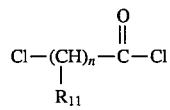   XXXII in the presence of a solvent such as trichloromethane and a base such as aqueous potassium carbonate. Employing sodium iodide, a base such as potassium carbonate, and a solvent such as acetonitrile, the compound XXXI may then be reacted with the compound

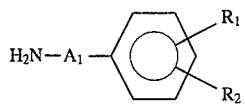   XIII to prepare the compound

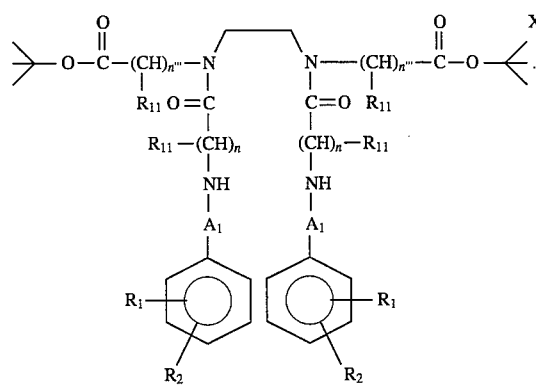   XXXIII

Reaction of the compound XXXIII with the compound

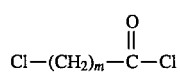   XXXIV in a solvent such as dimethylacetamide provides the compound:

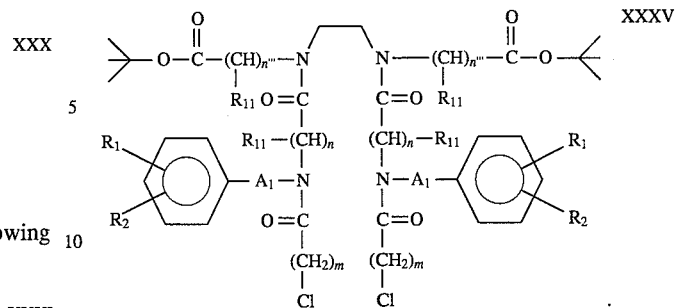   XXXV

The compound XXXV may then be employed in place of the compound III in Scheme A described below to provide the aforementioned dimer.

A similar procedure may be employed to prepare dimer compounds wherein one of the $R_{12}$ groups is

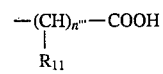

and the other is hydrogen. In such a case, monosubstituted ethylenediamine of the formula

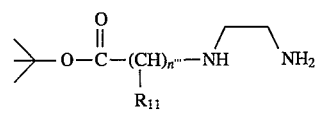

may be prepared by the reaction of ethylenediamine and the compound XXIX, and employed in place of the compound XXX in the method described above.

Multimers, such as any of those described above, may be particularly useful as blood pool agents. Such blood pool agents may be employed, for example, as diagnostic agents to ascertain the integrity of a vascular network and/or the presence of hematomas.

Preparation of Formulae I', I", I'" and I"" Compounds

Exemplary methods for the preparation of compounds of the formulae I', I", I'" and I"" are described following.

To prepare the compounds of formula I', a compound of the formula IIa

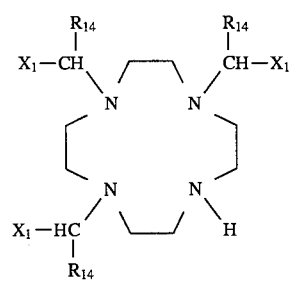

may be reacted in a solvent, e.g., water, and in the presence of a base, e.g., sodium hydroxide, with a compound of the formula

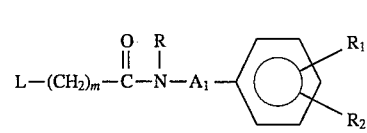   III wherein L is a leaving group, such as halogen. The starting compounds of the formula IIa may be prepared by known methods, such as those described in U.S. Pat. No. 4,885,363 to Tweedle et al. For example, in preparing compounds of formula IIa, reaction of a compound of the formula

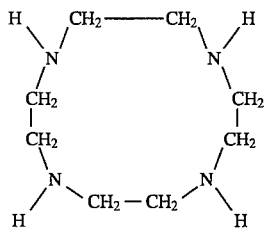

with a compound of the formula

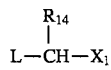

wherein L is a leaving group such as halogen, tosylate or triflate is preferably carried out in water at a pH of about 8.5 to 9, and the temperature of the reaction maintained at about 45°–55° C. Preferably, only about two equivalents of a compound of formula V are initially used in the reaction; an additional equivalent of the compound of formula V is added in portions starting about 2 to 3 hours after the reaction begins. The total reaction time will preferably be about 8 to 24 hours. The desired trisubstituted product can be separated from the reaction mixture, which includes the mono-, di-, tri- and tetra-substituted derivatives, by techniques recognized in the art including selective precipitation, chromatography and crystallization. For compounds where $X_1$ is $PO_3HY_1$, the method of Tazaki et al., Chem. Lett., 571 (1982), incorporated herein by reference, may be employed. An aminophosphonate group may be formed, for example, by contacting a tetraazacyclododecane compound, where at least one of the nitrogens of the tetraazacyclododecane ring bears a hydrogen, with formaldehyde, hydrochloric acid and phosphorus acid ($P(OH)_3$) to form one or more groups —$CH_2$—$P(O)(OH)_2$.

A preferred method for the preparation of the compounds of formula IIa wherein $R_{14}$ is hydrogen is to react 1,4,7,10-tetraazacyclododecane, known in the art, with dimethylformamidedimethylacetal in the presence of benzene to yield 1,4,7,10-tetraazatricyclo-[5.5.1.0]tridecane. This "tricyclic" compound is reacted with an ethanol/water mixture to yield 1-formyl-1,4,7,10-tetraazacyclododecane. This formyl compound is then reacted with t-butyl bromoacetate to yield 1-formyl-4,7,10-triscarboxymethyl-1,4,7,10-tetraazacyclododecane, tris-t-butylester. Finally, the ester groups are removed in the presence of strong acid, such as sulfuric acid, to yield a compound of formula IIa wherein $R_{14}$ is hydrogen. The most preferred methods for the preparation of formula IIa compounds are included in Dischino, et al., Inorg. Chem., 30, 1265, 1991.

The compounds of the present invention may also be prepared using the following Schemes.

Scheme A

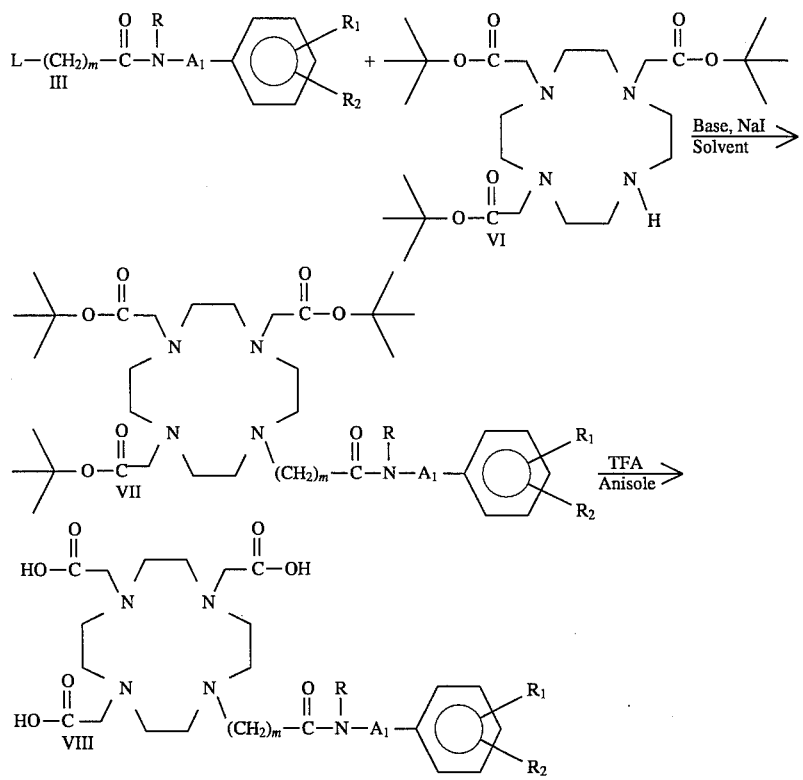

Scheme A is especially suitable for compounds of the formula I' where N-atoms 1, 4 and 7 in the tetraazacyclododecane nucleus have acetic acid moieties and particularly where R is also an acetic acid moiety. Compounds III and VI are reacted in the presence of a base, e.g., potassium or sodium carbonate, and sodium iodide and in a solvent, e.g., acetonitrile or dimethylacetamide and water, and preferably also in the presence of N,N-diisopropylethylamine, to provide intermediates of formula VII. The starting compound of the formula VI may be prepared by methods such as those described in Scheme F below. Compound VII is thereafter treated with, for example, a mixture of trifluoroacetic acid ("TFA") and anisole, to provide the products of formula VIII.

dium/carbon under an inert atmosphere such as nitrogen or argon in the presence of, for example, 1,4-cyclohexadiene as a hydrogen source in a solvent, e.g., methanol, and heat to provide intermediate XI. Reaction with compound XII in the presence of a base, e.g., potassium carbonate, and in the presence of a solvent, e.g., acetonitrile, provides the intermediate compound VII'. The compound VII' can be treated as in Scheme A (TFA, anisole) to provide the corresponding products VIII'.

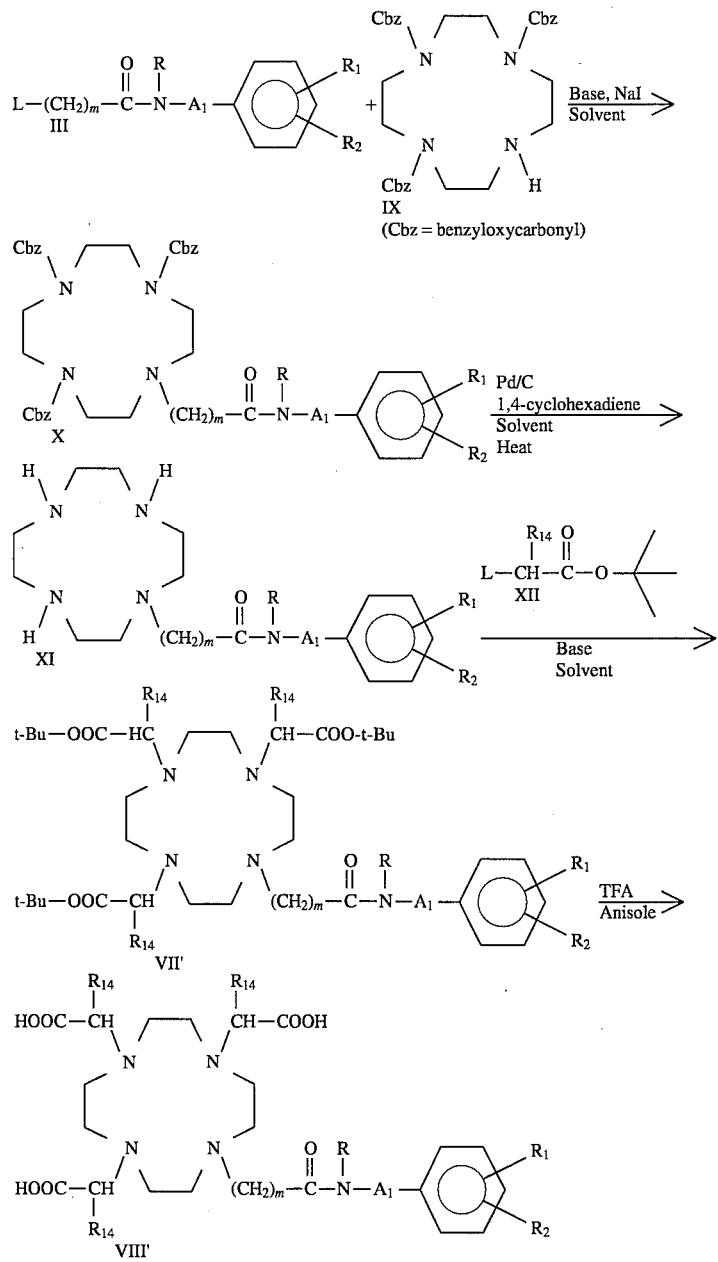

Scheme B provides a variation of Scheme A by employing the 1,4,7 benzyloxycarbonyl starting material of the formula IX which is reacted with compound III under conditions similar to Scheme A. The resulting intermediate X is then subjected to reducing conditions, e.g., treatment with palladium/carbon under an inert atmosphere such as nitrogen or The following Schemes describe additional procedures which may be used to obtain compounds of the present invention, or which may be used to prepare intermediates thereof.

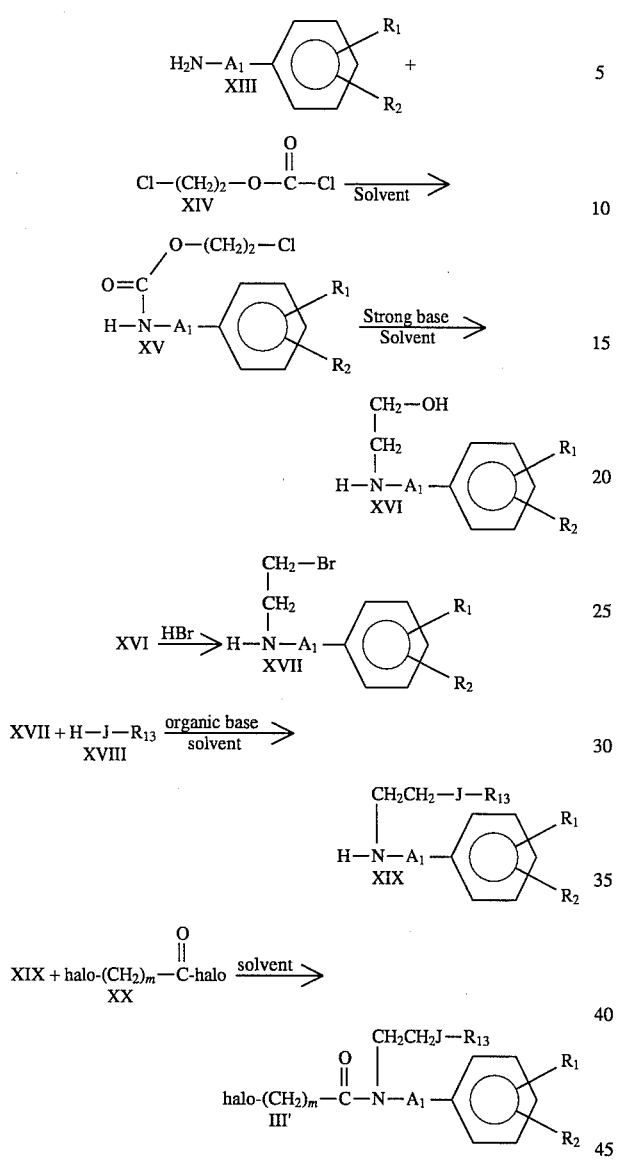

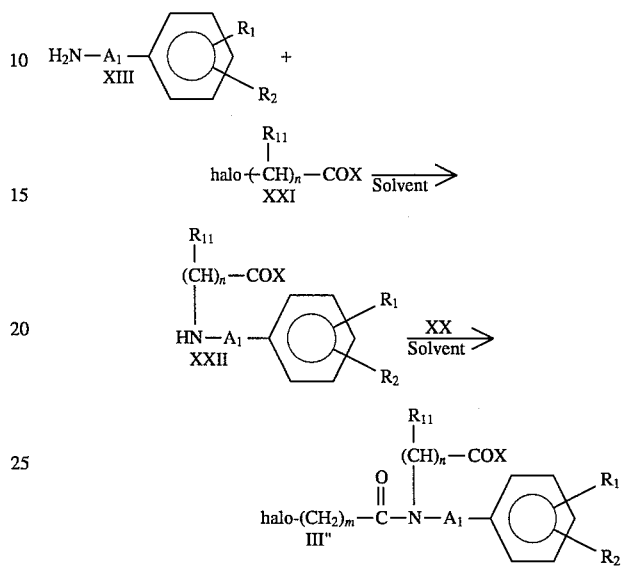

pound XIX in a solvent, e.g., dimethylacetamide, with the haloacetyl halide XX, provides the corresponding compounds of formula III'. (Where J is a protected amine group, J may be converted to —NH— subsequent to coupling with the segment Q and deprotection of all protecting groups.)

Scheme C illustrates the preparation of compounds of formula III where R is —[(CH$_2$)$_2$—Y]—R$_{13}$, designated herein as III'. This is more specifically illustrated in, inter alia, Example 10. This method is particularly suitable where one of R$_1$ and R$_2$ is hydrogen and the other is cycloalkyl. An amine XIII is reacted in, for example, dimethylacetamide, with a chloroformate of formula XIV to provide the carbamate of formula XV. Compounds of the formula XIII may be prepared by methods such as those described in Scheme E below. Carbamate XV is thereafter treated with a strong base, e.g., potassium hydroxide, in a solvent, e.g., ethanol, to provide the aniline of formula XVI. Treatment of XVI with an acid, e.g., HBr, provides compounds of formula XVII which can thereafter be reacted with a compound of formula XVIII where J denotes an oxygen atom or a protected amine group (i.e., —N(protecting group)-), preferably where the protecting group is benzyl. The reaction with the compound XVIII is conducted in a solvent, e.g., acetonitrile, and in the presence of an organic base, e.g., diisopropylethylamine, when J is a protected amine or an oxygen atom, or an inorganic base, e.g. NaH, when J is an oxygen atom, to provide the intermediate of formula XIX. Reaction of com- Scheme D illustrates the preparation of intermediates of formula III where R=

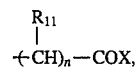

designated herein as III". Amine XIII is reacted with a compound of formula XXI in a solvent, e.g., dimethylacetamide or ethanol, to provide intermediate XXII. Intermediate XXII is thereafter reacted with a haloacetyl halide XX in a solvent, e.g., methylene chloride or dimethylacetamide, to yield the corresponding compounds of formula III".

Compounds of the formula III where R is

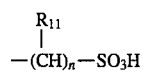

may be prepared by a method similar to Scheme D, wherein a compound of the formula:

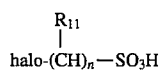

preferably in salt form, is employed in place of the compound XXI.

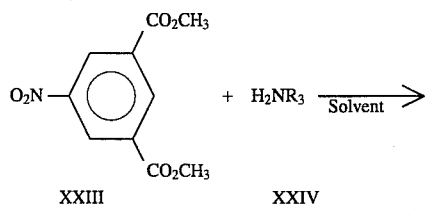

Scheme E -continued

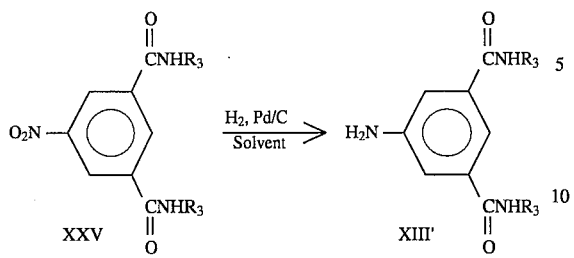

Scheme E illustrates the preparation of intermediates of formula XIII where $R_1$ and $R_2$ are each

and $A_1$ is a single bond designated herein as XIII'. Compound XXIII in a solvent, e.g., methanol, is reacted with amine XXIV to provide bisamide XXV which is thereafter reduced, e.g., with $H_2$ in the presence of a palladium/carbon catalyst, preferably in a dilute mineral acid, e.g. hydrochloric acid, to provide the amines of formula XIII where $R_1$ and $R_2$ are each

(XIII'). Any hydroxyl moieties within $R_3$ can be protected and deprotected by known methodology in the above reactions.

Scheme F

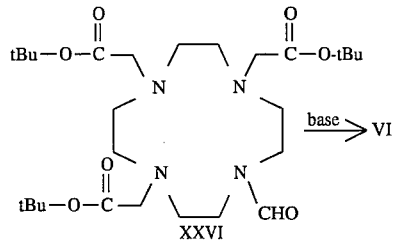

Scheme F illustrates the preparation of the compound of formula VI used in Scheme A. This compound is prepared by treatment of a compound of formula XXVI with a base, e.g., hydroxylamine, in a solvent, e.g., ethanol. Compound XXVI can be prepared as described by Dischino et al., *Inorg. Chem.*, 1991, 30, 1265–1269.

Scheme G

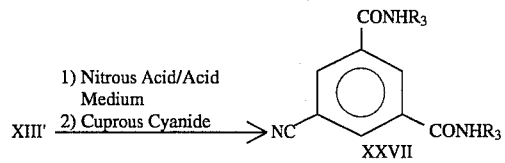

Scheme G -continued

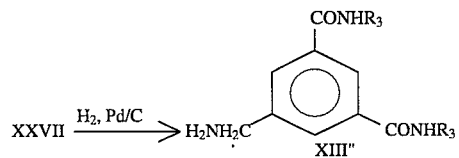

Scheme G provides methodology (described more generally in Scheme J) particularly suitable for preparing intermediates of the formula III where $A_1$ is $-CH_2-$, and where $R_1$ and $R_2$ are 3- and 5-position $-CONHR_3$ groups. A compound of the formula XIII' is diazotized, e.g., with nitrous acid in an acidic medium and thereafter treated with cuprous cyanide to provide the compound XXVII. Nitrile XXVII is then reduced, e.g., by treatment with gaseous $H_2$ in the presence of a palladium on carbon catalyst to provide compounds of formula XIII". Intermediates of the formula XIII" can then be used as compound XIII for the preparation of compounds of the formula III as described in the Schemes above to provide the desired products where $A_1$ is $CH_2$.

Scheme H

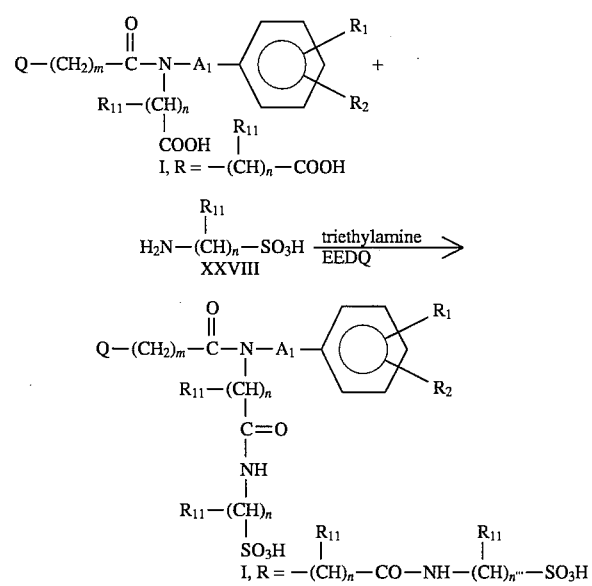

Scheme H illustrates the preparation of compounds of the formula I where R is

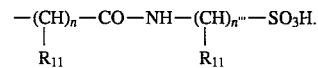

In this method, starting compound of the formula I where R is

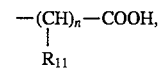

or preferably, such a compound in salt form (especially where R is

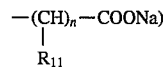

where Q is complexed with a metal such as gadolinium, is contacted with compound XXVIII in the presence of an amine such as triethylamine and N-ethoxycarbonyl-2-ethoxy-1,2-dihydroquinoline ("EEDQ"). The amine salt formed may then be converted to the free sulfonic acid.

Scheme I

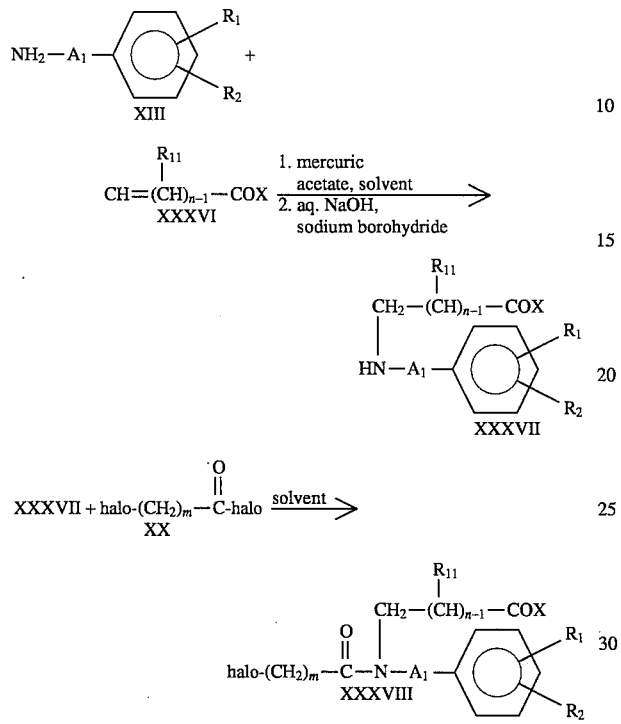

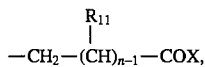

Scheme I illustrates preparation of compounds of the formula III where R is $$-CH_2-(CH)_{n-1}-COX,$$
$$\phantom{-CH_2-(CH)_{n-1}}|$$
$$\phantom{-CH_2-(CH)_{n-1}}R_{11}$$

designated "XXXVIII" above. In this method, amine XIII is contacted with olefin XXXVI and treated with mercuric acetate in a solvent such as tetrahydrofuran, followed by treatment with aqueous sodium hydroxide and sodium borohydride. The compound XXXVII obtained is then contacted with compound XX, in a solvent such as dimethyl acetamide, to yield the compound XXXVIII.

Scheme J

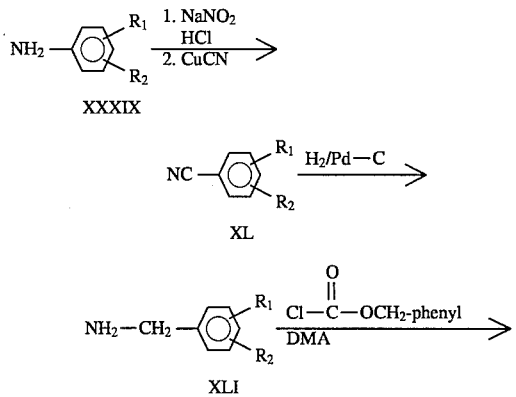

Scheme J

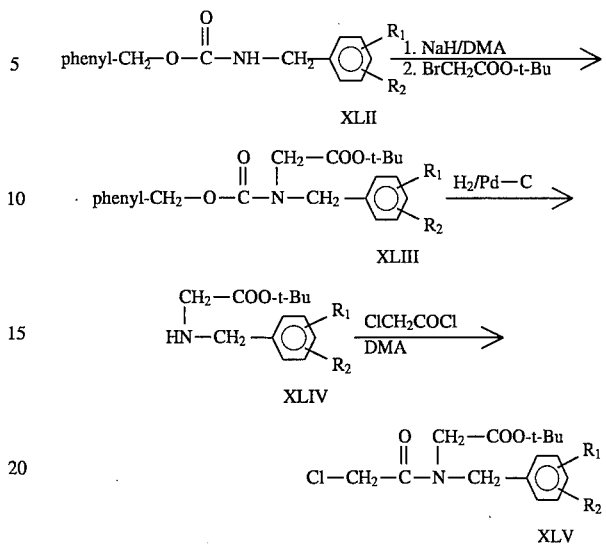

Scheme J illustrates preparation of compounds of the formula XLV, which are compounds of the formula III where $A_1$ is —$CH_2$— and R is —$CH_2$—COO-t-Bu, and which may be used as described above. According to Scheme J, an aniline compound XXXIX may be diazotized such as by treatment with $NaNO_2$ and HCl, followed by treatment with cuprous cyanide to form compound XL. Reduction of compound XL, e.g., by treatment with $H_2$ gas in the presence of a palladium on carbon catalyst, provides compound XLI, which may be treated with benzylchloroformate to prepare compound XLII. Treatment of compound XLII at low temperature (e.g., −10° C.) with a base such as sodium hydride, followed by $BrCH_2COO$-t-Bu provides compound XLIII, which may be reduced, e.g., by treatment with $H_2$ gas in the presence of a palladium on carbon catalyst, to compound XLIV. Compound XLV may then be prepared by treatment of compound XLIV with $ClCH_2COCl$. A solvent such as dimethylacetamide may be employed for the aforementioned reactions as indicated.

Scheme K

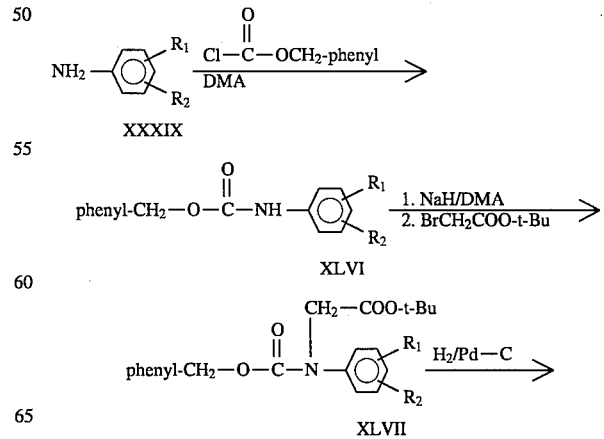

-continued
Scheme K

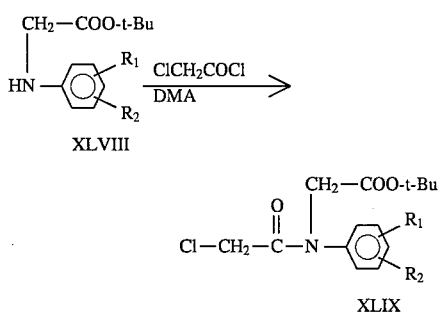

Scheme K illustrates preparation of compounds of the formula XLIX, which are compounds of the formula III where $A_1$ is a single bond and R is $-CH_2-COO$-t-Bu, and which may be used as described above. According to Scheme K, an aniline compound XXXIX may be reacted with benzylchloroformate to prepare compound XLVI. Treatment of compound XLVI at low temperature (e.g., $-10°$ C.) with a base such as sodium hydride, followed by $BrCH_2COO$-t-Bu provides compound XLVII, which may be reduced, e.g., by treatment with $H_2$ gas in the presence of a palladium on carbon catalyst, to compound XLVIII. Compound XLIX may then be prepared by treatment of compound XLVIII with $ClCH_2COCl$. A solvent such as dimethylacetamide may be employed for the aforementioned reactions as indicated.

Compounds of the formulae I'', I''' and I'''' may be similarly prepared by reacting the various compounds of formula III in a solvent, e.g. water, and in the presence of a base, e.g., sodium hydroxide with the corresponding compounds

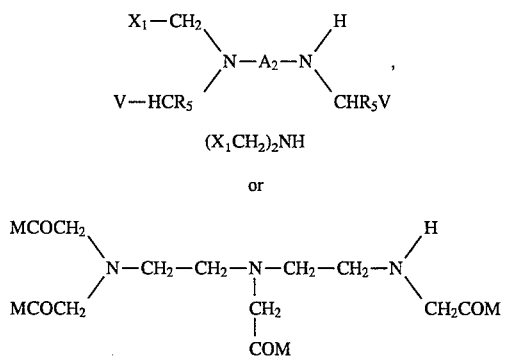

Compounds of the formulae IIb and IIc are described in U.S. Pat. No. 4,647,447. Compounds of the formula IId are described in U.S. Pat. No. 4,859,451.

Other compounds of the formula I may be prepared by procedures analogous to those described above for the preparation of compounds of the formulae I', I'', I''' and I'''', especially, by reaction of a compound QH with a compound of the formula III.

Preferred compounds of the present invention are those where $A_1$ is $-(CH_2)_2-$, or, especially, is a single bond. Particularly preferred compounds of the present invention are those wherein:

m is 1;

$A_1$ is a single bond or $-(CH_2)_2-$;

R is $-CH_2-COOH$; and one of $R_1$ and $R_2$ is hydrogen and the other of $R_1$ and $R_2$ is selected from alkyl, aryl, or cycloalkyl. Also preferred are the compounds where $R_1$ and $R_2$ are both alkyl, aryl and/or cycloalkyl.

Most preferred are the compounds of formula I' wherein $X_1$ is $-COOH$;

$A_1$ is a single bond;

R is $-CH_2COOH$;

$R_{14}$ is hydrogen;

m is 1; and $R_1$ and $R_2$ are each alkyl, which is especially preferred (particularly where $R_1$ and $R_2$ are both t-butyl), or one of $R_1$ and $R_2$ is hydrogen and the other is selected from phenyl or cyclohexyl.

All stereoisomers, geometric isomers, atropoisomers and conformational isomers of the compounds and complexes of the present invention are contemplated herein, whether alone (that is, substantially free of other isomers), in a mixture of certain isomers (for example, as a racemate) or in any other mixture thereof.

The invention will now be further described by the following examples, but is not limited to the details therein.

EXAMPLE 1

10-[2-[(Carboxymethyl)-(4-methylphenyl)amino]-2-oxoethyl]-1,4,7,10-tetraazacyclododecane-1,4,7-triacetic acid ("MPA-DO3A")

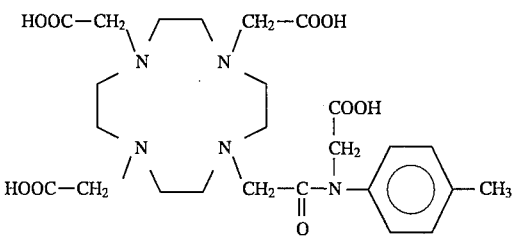

A. N-(p-Tolyl)-glycine-(1,1-dimethylethyl)ester

A solution of t-butyl bromoacetate (29.3 g) and p-toluidine (48.2 g) in absolute ethanol (EtOH) (50 mL) was stirred under nitrogen at ambient temperature. After 30 minutes, a copious precipitate formed. The reaction mixture was concentrated in vacuo, and the residue was treated with 300 mL of ethyl ether ($Et_2O$), stirred for 30 minutes, and filtered. The filtrate was concentrated in vacuo to afford 50 g of crude product. The material was partially purified on a silica gel column to afford 34.0 g of the product as a brown oil. This material was distilled in vacuo. The fraction boiling at $105°$–$110°$ C. at a pressure of 0.35–0.45 mm was collected to afford purified title A compound (18.7 g) as a pale yellow oil.

Microanalysis calc'd for $C_{13}H_{19}NO_2$: C, 70.56; H, 8.65; N, 6.33; O, 14.46%; Found: C, 70.18; H, 8.63; N, 6.31%.

B. N-[(Chloroacetyl)-N-(p-tolyl)]-glycine-(1,1-dimethylethyl)ester

A solution of the title A amine (15.9 g) in dry dimethylacetamide (500 mL) was treated with chloroacetyl chloride (16.2 g) in one portion, and the reaction was stirred stoppered at ambient temperature. At the end of the reaction the solvent was concentrated in vacuo. The residue was partitioned between saturated $NaHCO_3$ and ethyl acetate (EtOAc). The organic layer was dried ($MgSO_4$), and the solvent was removed in vacuo to afford 16.8 g of the title B compound.

Microanalysis calc'd for $C_{15}H_{20}NO_3Cl$: C, 60.50; H, 6.77; N, 4.70; Cl, 11.91; O, 16.12%; Found: C, 60.60; H, 6.85; N, 4.60; Cl, 11.75%.

C. 1,4,7,10-Tetraazacyclododecane-1,4,7-tricarboxylic acid, tris(phenylmethyl) ester A solution of benzyloxychloroformate (110 mL) in 100 mL dry CHCl₃ was added dropwise to a solution of dry 1,4,7,10-tetraazacyclododecane (43.07 g) in 2.00 L dry CHCl₃ and 108 mL triethylamine (776 mmol) maintained at −5° C. under a dry nitrogen atmosphere. At 20.5 hours, the cold solution was extracted with 2×250 mL dilute HCl (pH 1), washed with 4×250 mL water, then 2×250 mL saturated NaHCO₃. The organic layer was dried over MgSO₄, then evaporated to an oil. The crude was purified on a 11×44 cm (2.5 kg) silica gel flash column (65:35 hexane:ethyl acetate) using a step gradient of hexane:ethyl acetate. The by-product 1,4,7,10-tetraazacyclododecane-1,4,7,10-tetracarboxylic acid, tetrakis(phenymethyl) ester was eluted at an ethyl acetate:hexane composition of 7:3 and the title C 1,4,7,10-tetraazacyclododecane-1,4,7-tricarboxylic acid, tris(phenymethyl) ester was eluted between a composition of 8:2 and 85:15 ethyl acetate:hexane. The yield of title product C was 48.85 g.

Elemental analysis calc'd for $C_{32}H_{38}N_4O_6$: C, 66.88; H, 6.66; N, 9.75; Found: C, 66.88; H, 6.85; N, 9.66.

D. 10-[2-[N-(4-Methylphenyl)-N-[(1,1-dimethylethyl-carboxymethyl)amino]-2-oxoethyl]-1,4,7-benzyloxycarbonyl-1,4,7,10-tetraazacyclododecane A solution of the title C compound (15.6 g) and the title B chloroanilide (8.1 g) in acetonitrile (80 mL) under nitrogen was treated with powdered Na₂CO₃ (5.8 g, 54.4 mmol) followed by NaI (4.1 g, 27.2 mmol), and the reaction mixture was heated to reflux under nitrogen. After 24 hours, the reaction mixture was partitioned between EtOAc and H₂O. The organic layer was washed with brine and dried over MgSO₄. This gave 21.65 g of crude product. Flash chromatography on silica gel, afforded 17.2 g of pure title D compound as a white foam.

Microanalysis calc'd for $C_{47}H_{57}N_5O_9$: C, 67.53; H, 6.87; N, 8.38; O, 17.22%; Found: C, 67.36; H, 7.01; N, 8.35%.

E. 10-[2-[N-(4-Methylphenyl)-N-[(1,1-dimethylethylcarbóxymethyl)amino-2-oxoethyl]-1,4,7,10-tetraazacyclododecane A solution of the title D compound (15.9 g) in methanol (65 mL) under nitrogen was treated with 10% Pd/C (1.6 g) followed by 1,4-cyclohexadiene (15.2 g), and the reaction mixture was heated to reflux for 2.5 hours. The reaction mixture was cooled to ambient temperature and the suspension was filtered through celite. The filter pad was washed with EtOAc, and the combined filtrate was concentrated in vacuo to afford 8.3 g of the title E compound as a white foam.

Microanalysis calc'd for $C_{23}H_{39}N_5O_3 \cdot 0.17 \, H_2O$: C, 63.27; H, 9.08; N, 16.04; O, 11.61%; Found: C, 63.44; H, 9.04; N, 15.68; H₂O, 0.70%.

F. 10-[2-[N-(4-Methylphenyl)-N-(carboxymethyl)amino]-2-oxoethyl]-1,4,7,10-tetraazacyclododecane-1,4,7-triacetic acid, tetrakis-(1,1-dimethylethyl) ester A solution of the title E compound (7.5 g) in 55 mL of acetonitrile under nitrogen was treated sequentially with powdered K₂CO₃ (19.0 g), and t-butyl bromoacetate (11.1 g). The reaction mixture was heated at 50° C. under nitrogen for 24 hours. The solids were filtered; the filtrate was concentrated in vacuo, and the residue was partitioned between EtOAc and H₂O. The organic layer was washed with brine and dried over Na₂SO₄ to afford 12.8 g of the title F compound as a reddish-brown foam. This product was used, without purification, for the next reaction.

G. 10-[2-[(Carboxymethyl)-(4-methylphenyl)amino]-2-oxoethyl]-1,4,7,10-tetraazacyclododecane-1,4,7-triacetic acid A solution of the title F compound (5.0 g) in trifluoroacetic acid (TFA) (200 mL) and anisole (20 mL) was allowed to stir for 1 hour at ambient temperature under nitrogen. This solvent was removed in vacuo, and the residue was partitioned between Et₂O and H₂O. The aqueous layer was concentrated in vacuo to afford 6.9 g of the crude bis TFA salt as a dark brown oil. This was desalted by a cation exchange column procedure to obtain 2.9 g of the presumed bis-ammonium salt as a brown foam. This product was purified by anion exchange chromatography to obtain the triethylammonium salt of the title compound. The free acid form of this product was obtained by passage through an anion exchange resin and elution with dilute formic acid. The title G compound was isolated as a foamy solid (1.23 g).

Microanalysis calc'd for $C_{25}H_{37}N_5O_9 \cdot 0.6H_2O$: C, 53.40; H, 6.85; N, 12.45; O, 27.30%; Found: C, 53.11; H, 6.97; N, 12.17; H₂O, 1.91%.

EXAMPLE 1A

10-[2-N-(4-Methylphenyl)-N-(carboxymethyl)amino]-2-oxoethyl]-1,4,7,10-tetraazacyclododecane triacetic acid monogadolinium monosodium salt (or free acid) ("Gd-MPA-DO3A")

The title chelate was prepared according to the method of Example 3A, except that the title compound of Example 1 was employed in place of the title compound of Example 3 and $^{153}GDCl_3$ was employed in place of GdCl₃.

The HPLC conditions employed for the purification of the title chelate were: Retention time: 7.8 min. Column: Hamilton PRP-1 reverse phase 25 cm×4.1 mm i.d. Elution conditions: 10% CH₃CN 90% aqueous buffer consisting of 10 mM disodium EDTA and 50 mM tris acetate adjusted to pH=7.4. Flow rate: 1.0 mL/min. Detection: Radioisotope detection.

EXAMPLE 2

10-[2-[(Carboxymethyl)]-4-(1,1-dimethylethyl) phenyl]amino]-2-oxoethyl]-1,4,7,10-tetraazacyclododecane-1,4,7-triacetic acid ("BPA-DO3A")

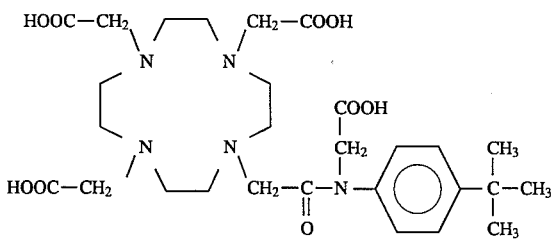

A. tert-Butyl-[N-(4-tert-butylphenyl)]glycinate 4-tert-Butylaniline (22.39 g) was added to absolute ethanol (25 mL) and the mixture was stirred at 0° C. tert-Butyl bromoacetate (9.75 g) was added via syringe over a 5 minute period. The mixture was stored at 0° C. overnight and then the volatiles were removed by rotary evaporation. Ether was added to the residue and the mixture was stirred 0.5 hours at 0° C. The resulting precipitate was vacuum filtered. The ether was removed from the filtrate by rotary evaporation to give 19.5 g of the crude isolate as an oil.

The mixture was purified by silica gel flash chromatography. This gave 13.2 g of the title A product as a pale orange oil contaminated with very small amounts of the starting aniline. The oil was distilled at 0.10 mm Hg using a short path apparatus; two fractions were collected. Fraction 1: b.p. 100°–110° C. @ 0.10 mm Hg, 1.52 g; Fraction 2: b.p.

110°–113° C. @ 0.10 mm Hg, 10.35 g. The material obtained from fraction 2 was used in the next step.

Microanalysis calc'd for $C_{16}H_{25}NO_2$: C, 72.97; H, 9.57; N, 5.32; O, 12.15; Found: C, 73.21; H, 9.57; N, 5.48; O, 11.74.

B. tert-Butyl-[N-(chloroacetyl), N-(4-tert-butylphenyl)]glycinate

A flask containing nitrogen was charged with N,N-dimethylacetamide (140 mL) and the title A compound (9.68 g, as a solution in 10 mL of N,N-dimethylacetamide). The mixture was stirred at ambient temperature and chloroacetyl chloride (8.30 g) was added. The mixture was stirred for 1 hour at ambient temperature.

The solvents were removed in vacuo and the residue was partitioned between ethyl acetate and aqueous $NaHCO_3$ solution. The organic layer was washed with saturated brine and dried over $Na_2SO_4$. The solvents were removed in vacuo to provide 12.41 g of crude compound, which was recrystallized from ethyl acetate/hexanes. This afforded 10.4 g of the title B compound as a white solid, (m.p. 156.8°–157.8° C.).

Microanalysis calc'd for $C_{17}H_{26}NO_3Cl$: C, 63.61; H, 7.71; N, 4.12; Cl, 10.43; O, 14.12%; Found: C, 63.67; H, 7.73; N, 4.13; Cl, 10.32%.

C. 10-[2-[N-(4-tert-Butylphenyl)-N-(t-butoxycarbonylmethyl)amino]-2-oxoethyl]-1,4,7-tris(benzyloxycarbonyl)-1,4,7,10-tetraazacyclododecane A flask was charged with the title C compound of Example 1 (5.75 g), anhydrous, finely powdered $Na_2CO_3$ (2.10 g), the title B compound (3.398 g) and acetonitrile (10 mL). The mixture was stirred until the organic components dissolved and then sodium iodide (1.50 g, dissolved in 15 mL of acetonitrile) was added. The mixture was kept at reflux for 23 hours. The salts were filtered and the volatiles were removed by evaporation. The resulting residue was partitioned between ethyl acetate and water. The organic layer was washed with half-saturated brine and then with saturated brine. The organic layer was dried over $Na_2SO_4$. Removal of the volatiles gave 8.82 g of a crude foam. Purification by silica gel flash chromatography provided 7.58 g of the title C compound as a white foam.

Microanalysis calc'd for $C_{50}H_{63}N_5O_9$: C, 68.39; H, 7.23; N, 7.98; O, 16.40%; Found: C, 68.50; H, 7.34; N, 7.92%.

D. 1-[2-[N-(4-tert-Butylphenyl)-N-(t-butoxycarbonylmethyl)amino]-2-oxoethyl]-1,4,7,10-tetraazacyclododecane A flask was charged with 10% palladium on carbon (5.0 g) and the title C compound (5.0 g) dissolved in $CH_3OH$ (50 mL) was added. Cyclohexadiene (13.12 g) was introduced via syringe to the stirred solution and the mixture was heated at reflux for 40 minutes. The catalyst was filtered through Celite 545 under a blanket of nitrogen. Evaporation of the volatiles gave 2.51 g of the title D compound as a white foam.

Microanalysis calc'd $C_{26}H_{45}N_5O_3 \cdot 0.31 H_2O \cdot 0.20 CH_3OH$: C, 64.53; H, 9.59; N, 14.36; O, 11.52%; Found: C, 63.64; H, 9.32; N, 14.01%.

E. 10-[2-[N-(4-tert-Butylphenyl)-N-(tert-butoxycarbonylmethyl)amino]-2-oxoethyl]-1,4,7-(t-butoxycarbonylmethyl)-1,4,7,10-tetraazacyclododecane A flask was charged with the title D product (3.026 g), acetonitrile (HPLC grade, 14.5 mL), and anhydrous potassium carbonate (4.98 g). The mixture was stirred at 50° C. and tert-butylbromoacetate (2.92 g) was added via syringe over a period of 5 minutes. The mixture was stirred at 50° C. for 1 hour. Additional tert-butylbromoacetate (0.603 g) was added and the mixture was stirred 2 hours at 50° C. and then at ambient temperature overnight. The mixture was diluted with 200 mL of acetonitrile and the salts were filtered through Celite 545. The volatiles were removed from the filtrate and the residue was pumped on at high vacuum to give 5.86 g of a crude yellow foam which was used directly in the next step.

F. 10-[2-[(Carboxymethyl)[4-(1,1-dimethylethyl)phenyl]amino]-2-oxoethyl]-1,4,7,10-tetraazacyclododecane-1,4,7-triacetic acid A flask was charged with trifluoroacetic acid (118.4 g), anisole (7.96 g) and the title E tetratert-butyl ester (2.00 g). The mixture was stirred for 2.75 hours at ambient temperature.

The volatiles were removed in vacuo to give a brown residue, which was dissolved in 50 mL of deionized water and extracted with ether (3×50 mL) and once with hexanes (50 mL). The resulting aqueous layer was pumped on at high vacuum with stirring to remove traces of organic solvents. Residual particulates were filtered off.

The resulting solution was desalted by passing through a cation exchange column to provide 1.23 g (1.96 mmoles) of the crude product as a yellow powder. This was further purified by anion exchange chromatography, which furnished 0.970 g of the bistriethylammonium salt of the product.

The triethylammonium salt was converted into the free acid by passage through an anion exchange column and elution with dilute formic acid. This procedure yielded the title compound (0.657 g, >99.7% purity).

Microanalysis calc'd for $C_{28}H_{43}N_5O_9$: C, 56.65; H, 7.30; N, 11.80; O, 24.25%; Found: C, 56.60, H, 7.47; N, 11.75%.

EXAMPLE 2A

10-[2-N-(4-t-Butylphenyl)-N-(carboxymethyl)amino-2-oxoethyl]-1,4,7,10-tetraazacyclododecane-1,4,7-triacetic acid monogadolinium monosodium salt (or free acid) ("Gd-BPA-DO3A")

The title chelate was prepared according to the method of Example 3A, except that the title compound of Example 2 was employed in place of the title compound of Example 3 and $^{153}GDCl_3$ was employed in place of $GdCl_3$.

HPLC conditions employed for the purification of the title chelate were: Retention time: 12.33 min. Column: Hamilton PRP-1 reverse phase 25 cm×4.1 mm i.d. Elution conditions: 20% $CH_3CN$ in 80% aqueous buffer consisting of 0.1 mM disodium EDTA and 0.5 mM tris-acetate adjusted to pH=7.4. Flow rate: 1.0 mL/min. Detection: Ultraviolet at 254 nm.

EXAMPLE 3

10-[2-[([1,1'-Biphenyl]-4-yl)(carboxymethyl)amino]-2-oxoethyl]-1,4,7,10-tetraazacyclododecane-1,4,7-triacetic acid ("PPA-DO3A")

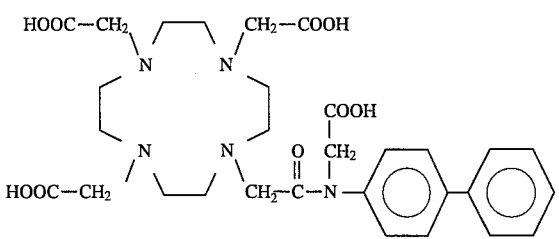

A. tert-Butyl-N-[(1,1'-biphenyl)-4-yl]glycinate

A flask was charged with 4-aminobiphenyl (22.0 g) and absolute ethanol (46.42 mL), and the mixture was stirred at ambient temperature until the amine dissolved. tert-Butylbromoacetate (8.448 g) was then added in four aliquots over a 2 minute period. The mixture was stirred for 2 hours at ambient temperature, 6 hours at 45° C. and finally 15 hours at ambient temperature.

The volatiles were removed on a rotary evaporator and ether (150 mL) was added to the residue. The mixture was stirred 0.5 hour at ambient temperature and 2 hours at 0° C. The solids were removed by filtration and the filter cake was washed with ether (3×50 mL). Examination of the filter cake showed that it did not contain any of the desired product. The volatiles were removed from the combined ether layers to give 14.68 g (119.7% crude yield) of a dark red solid.

This was purified by silica gel flash chromatography using hexanes/ethyl acetate 8/1 v/v as the eluent. Fractions 7–9 were contaminated with the starting material and thus only fractions 10–21 were combined. Evaporation of the volatiles afforded 10.28 g (83.8% yield) of the desired product contaminated with a small amount of the starting 4-aminobiphenyl.

The compound obtained from the prior chromatography was adsorbed onto 32 g of silica gel and purified by flash chromatography on a silica gel (1450 g) column using hexanes/ethyl acetate 10/1 v/v as the eluent. The flow rate was 150 mL/min and 70 mL fractions were collected. The desired product was obtained in fractions 56–110. Fractions 58–110 were pooled and the volatiles were evaporated to provide 8.28 g (67.54% yield) of the title A compound as white flakes (m.p. 83.1°–84.8° C.) contaminated with a trace amount of an orange colored impurity. An analytical sample recrystallized from hexanes gave the title A compound. m.p. 88.2°–89.2° C.

Microanalysis Calc'd for $C_{18}H_{21}NO_2$: C, 76.30; H, 7.47; N, 4.94; O, 11.29. Found: C, 76.30; H, 7.35; N, 5.24; O, 11.11.

B. tert-Butyl[N-(chloroacetyl),N-[1,1'-biphenyl)-4-yl)]glycinate

A flask was charged with the title A compound (6.16 g) and N,N-dimethylacetamide (86.0 mL, Aldrich anhydrous grade). The mixture was stirred at ambient temperature until the aminoester dissolved and chloroacetylchloride (4.90 g) was added dropwise via syringe over a 2 minute period. The mixture was stirred 3 hours and the volatiles were then removed by rotary evaporation at 50°–58° C. (0.1 mm Hg). The resulting residue was dissolved in 300 mL of dichloromethane and washed with half-saturated $NaHCO_3$ solution (200 mL). The organic layer was washed with distilled, deionized water (2×250 mL) and dried with saturated brine (2×150 mL) and powdered sodium sulfate.

The volatiles were removed to give 8.47 g of the crude chloroanilide as an orange solid. Purification of the solid was accomplished by recrystallization from ethyl acetate/hexanes. This afforded 5.8 g (74.4% yield) of the title B compound as pale yellow rhomboids. m.p.=106°–106.9° C.

Microanalysis: Calc'd for $C_{20}H_{22}ClNO_3$: C, 66.76; H, 6.16; N, 3.89; Cl, 9.85; O, 13.34. Found: C, 67.01; H, 6.19; N, 3.99; Cl, 9.99; O, 12.82.

C. 1,4,7,10-Tetraazacyclododecane-1,4,7-triacetic acid, tris(1,1-dimethylethyl) ester, monohydrochloride 1-Formyl-1,4,7,10-tetraazacyclododecane-1,4,7-triacetic acid, tris(1,1-dimethylethyl) ester (prepared as described in Dischino et al., *Inorg. Chem.*, 1991, 30, 1265–69) in anhydrous ethanol was treated with hydroxylamine hydrochloride at reflux under an atmosphere of argon for 18 hours. The reaction mixture was cooled and the volatiles were removed under reduced pressure. To the solid obtained, $CH_2Cl_2$ (1 L) was added. After washing with water (3×200 mL) and brine (3×200 mL), the organic phase was separated, dried over $Na_2SO_4$ and concentrated under reduced pressure to give a pale yellow solid (approximately 90 g). The solid was recrystallized twice from a mixture of $CH_2Cl_2$ and hexane, and dried in a vacuum oven at 35° C. for 18 hours to give 57 g of the title C compound.

Elemental analysis calc'd for $C_{26}H_{50}N_4O_6 \cdot HCl$: C, 55.21; H, 9.25; N, 9.84; Cl, 7.49; Found: C, 55.40; H, 9.43; N, 9.84; Cl, 7.48.

D. 10-[2-[[1,1'-Biphenyl-4-yl](1,1-dimethylethyloxycarbonylmethyl)amino]-2-oxoethyl]-1,4,7,10-tetraazacyclododecane-1,4,7-triacetic acid tris(1,1-dimethylethyl) ester A 125 mL separatory funnel was charged with distilled, deionized water (25 mL) and potassium carbonate (5.0 g). A flask was charged with the title C compound (5.50 g) and dichloromethane (25 mL); the mixture was stirred until the solution was homogenous. The aqueous solution of potassium carbonate was added dropwise over a short period to the stirring dichloromethane solution of the title C compound. Then the entire mixture was transferred to the separatory funnel. The mixture was diluted with distilled deionized water (10 mL) and dichloromethane (10 mL). The layers were separated and the aqueous layer was washed with dichloromethane (2×30 mL). The combined organic layers were dried for 5 hours over powdered anhydrous sodium sulfate. The drying agent was filtered and the volatiles were removed to give a white pasty solid. This was kept under high vacuum (0.1 mm Hg) for 12 hours at ambient temperature. The resulting solid (5.14 g) contained 1,4,7,10-tetraazacyclododecane-1,4,7-triacetic acid-tris(1,1-dimethylethyl) ester free base (100% yield).

The free base was mixed with acetonitrile (HPLC grade, 15 mL) and powdered, anhydrous potassium carbonate (3.45 g). The mixture was stirred several minutes and the title B compound (3.41 g) was added in one portion. The mixture was stirred for 5 minutes at ambient temperature; then, a solution of anhydrous sodium iodide (1.51 g) in acetonitrile (HPLC grade) was added all at once. The mixture was stirred for 4 hours at 56°–58° C. and for 13 hours at ambient temperature. The mixture was then diluted by addition of acetonitrile (150 mL) and the salts were filtered. The volatiles were removed by rotary evaporation and pumping at 0.1 mm Hg overnight, providing a yellow foam containing the title D compound (high yield conversion of the free base into the title compound D). (HPLC ret. time=3.997 min.)

E. 10-[2-[[1,1'-Biphenyl-4-yl]carboxymethyl)amino]-2-oxoethyl]-1,4,7,10-tetraazacyclododecane-1,4,7-triacetic acid A flask filled with dry nitrogen was charged with anisole (32 mL) and trifluoroacetic acid (320 mL). The mixture was stirred at ambient temperature and the title D compound (8.02 g) was added; residual material was washed in with anisole (2×5 mL). The mixture was stirred for 5.5 hours under nitrogen. The volatiles were removed with a water aspirator pump and then at high vacuum. The resulting yellow glass was pumped on at 0.10 mm Hg overnight. This gave 10.20 g of a bronze glass.

A 10 g portion of the glass was dissolved in 300 mL of distilled, deionized water, then ether (300 mL) was added and the entire mixture was swirled to dissolve remaining solids. The entire mixture was added to a separatory funnel and the ether layer was removed. The aqueous layer was washed with ether (3× 300 mL). The resulting aqueous layer was diluted with 200 mL of distilled deionized water. The resulting colorless, slightly turbid solution was pumped on with the aspirator pump on the rotary evaporator to remove ~50 mL of ether. The aqueous solution of the product (25 mL aliquots) was passed through 0.45µ filter disks to remove the turbidity. The filter disk was changed after each aliquot was filtered.

The resulting clear solution was applied to a 5.4 cm wide column of Bio-Rad AG50W-$X_2$ resin (cation exchanger). The column was eluted with distilled deionized water and then with 2.0M aqueous ammonia (70 mL fractions were collected). The product containing fractions were combined and the volatiles were removed to afford 5.10 g (98.3% of theoretical) of the bis ammonium salt of the product. HPLC analysis showed a purity of 84.5%.

The ammonium salt was dissolved in 500 mL of 0.005M aqueous triethylammonium bicarbonate solution and this solution was applied to a 30 cm×5.4 cm column of DEAE Sephadex A-25 anion exchange resin (bicarbonate form). After the solution of the compound was applied to the column the column was eluted with 520 mL of 0.005M aqueous triethylammonium bicarbonate solution. Then the column was eluted with a linear gradient using 0.005M triethylammonium hydrogen carbonate (4 L) as the low concentration component and 0.50M triethylammonium hydrogen carbonate (4 L) as the high concentration component. The product containing fractions were pooled and the volatiles were removed to give 5.50 g (84.19% yield) of the bis-triethylammonium salt of the title E compound as a white foam.

Microanalysis: Calc'd for $C_{42}H_{69}N_7O_9$: based on 0.51 wt % $H_2O$, C, 61.50; H, 8.54; N, 11.95; O, 18.00. Found: C, 61.11; H, 8.30; N, 11.77; O, 18.82.

A 5.20 g portion of the above bis-triethylammonium salt was dissolved in distilled, deionized water (400 mL) and this solution was applied to a 5.4 cm wide (400 g) column of Bio-Rad AG1-$X_2$ ion exchange resin (formate form). The column was eluted with ~6 L of distilled, deionized water until the conductivity was stable at 9.1 µS/cm. Then the eluent was changed to 2.0M aqueous formic acid and the collection of 75 mL fractions was initiated. Fractions 10–20 contained the desired product and these were pooled. Removal of volatiles by evaporation and lyophilization gave 3.91 g of the title E compound (82.5% yield based on input triethylammonium salt to the desired tetra-acid).

Microanalysis calc'd for $C_{30}H_{39}N_5O_9 \cdot 0.67\ H_2O \cdot 0.02\ Cl$: C, 57.52; H, 6.49; N, 11.18; Cl, 0.11; O, 24.73; Found: C, 57.92; H, 6.52; N, 11.19; Cl, 0.12; O, 24.25.

EXAMPLE 3A

10-[2-[([1,1'-Biphenyl]-4-yl)(carboxymethyl)amino]-2-oxoethyl]-1,4,7,10-tetraazacyclododecane-1,4,7-triacetic acid monogadolinium monosodium salt ("Gd-PPA-DO3A")

The title chelate was prepared from the reaction of the title compound of Example 3 (0.06194 gm) and $GdCl_3$ (0.1 mmol). Both reactants were mixed in a small vial and the pH of the reaction mixture was raised very slowly, while the mixture was heated at 80° C. The crude material was purified by semipreparative HPLC. The major peak was collected. All of the fractions were collected, combined, and dried by rotory evaporation. The solid material (69 mg, 87.3% yield) isolated was dried under vacuum at 60° C. to yield the title product.

Mass spectrum (FAB+): m/e=791 (M+H)$^+$, 791 (M+Na)$^+$. Microanalysis: Calc'd for $C_{30}H_{35}N_5O_9GdNa \cdot 3H_2O$ C, 42.69; H, 4.86; N, 8.28. Found: C, 42.72; H, 4.95; N, 8.28.

EXAMPLE 4

10-[2-[(2-Carboxymethyl)[2,5-di-tert-butylphenyl)amino]-2-oxoethyl]-1,4,7,10-tetraazacyclododecane-1,4,7-triacetic acid ("2,5-BPA-DO3A")

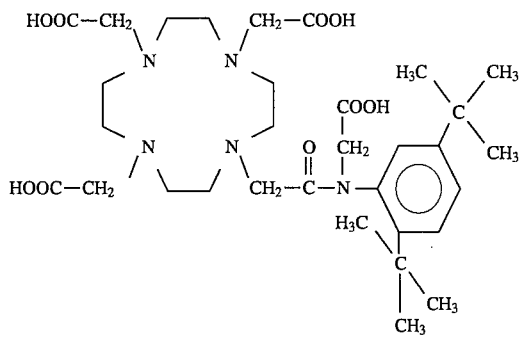

A. tert-Butyl[(N-chloroacetyl)-2,5-bis tert-butylphenyl)]glycinate

The title compound was prepared using the methodology of steps A and B of Example 3, except that 2,5-di-(tert-butyl)aniline was employed in place of 4-aminobiphenyl.

B. 10-[2-[(2-Carboxymethyl)[2,5-di-tert-butylphenyl)amino]-2-oxoethyl]-1,4,7,10-tetraazacyclododecane-1,4,7-triacetic acid A dry 250 mL round bottomed flask was charged with 1,4,7,10-tetraazacyclododecane-1,4,7-triacetic acid tris t-butyl ester (Example 3, 16.73 g), the title A compound (11.50 g), N,N-dimethylacetamide (97.5 mL), N,N-diisopropylethylamine (3.84 g), distilled, deionized water (1.0 mL), potassium carbonate (10.24 g) and sodium iodide (4.35 g) under a nitrogen atmosphere.

The mixture was vigorously agitated and then stirred at 85° C. for 65 hours using a reflux condenser to contain vapors. Then the mixture was cooled to ambient temperature and the salts were filtered. The volatiles were removed to give 31.71 g of a crude alkylate as a brown glass. The alkylate was added to a 2000 mL flask containing a well-stirred mixture of trifluoroacetic acid (750 mL) and anisole (75 mL) at ambient temperature under a nitrogen atmosphere. The mixture was stirred for 20 hours and the liquid phase was decanted into another 2000 mL flask. Then the volatiles were removed to provide a brown glass. This was purified by ion exchange chromatography to give the title product (11.20 g, 59.51% yield) as a white lyophilizate.

Mass Spectrum: (pos ion FAB) 650 (M+H)$^+$, 606 (M+H)$^+$—$CO_2$, 592 (M-$C_4H_{10}$)$^+$. Microanalysis: Calc'd for $C_{32}H_{51}N_5O_9 \cdot 0.43\ H_2O$ (found by Kf titration) C, 58.45; H, 7.95; N, 10.65. Found: C, 58.28; H, 8.04; N, 10.49.

EXAMPLE 4A

10-[2-[(2-Carboxymethyl)[2,5-di-tert-butylphenyl]amino]-2-oxoethyl]-1,4,7,10-tetraazacyclododecane-1,4,7-triacetic acid monogadolinium monosodium salt ("Gd-2,5-BPA-DO3A")

A 250 mL round bottomed flask equipped with a magnetic stir bar and a septum-capped inlet was charged with the title compound of Example 4 (9.17 g) and distilled deionized water (172 mL) and the pH was adjusted with aqueous 1.0M NaOH solution to ~5.5–6.0. Then gadolinium acetate tetrahydrate (6.877 g) was added all in one portion and the mixture was stirred at 70°–75° C. for 24 h. The mixture was cooled to ambient temperature and excess gadolinium was removed by precipitation with sodium hydroxide solution. The resulting product was purified by reverse phase column chromatography using a water-ethanol gradient elution (0–80% ethanol). The title compound was obtained as two (major and minor) conformational isomers. The major conformer (9.62 g, 82.4% yield) and minor conformer (1.09 g, 9.34%) were obtained as white fluffy lyophilizates.

Mass Spectrum

Major conformer: (MF-FAB pos., DDD, G) 846–851 cluster (M-H+2Na)⁺, 824–829 (M+Na)⁺, 802–807 (M+H)+ Minor conformer: (MF-FAB pos., TGG) 846–851 cluster (M-H+2Na)⁺, 824–829 (M+Na)⁺, 802–807 (M+H)⁺

Microanalysis

Major Conformer: Calc'd. for $C_{32}H_{47}N_5O_9GdNa \cdot 0.63 H_2O$: C, 45.92; H, 5.81; N, 8.37. Found: C, 44.87%; H, 5.94%; N, 8.21%. The KF value for water was found to be 0.63 moles (1.36 wt. %) which reflects unbound $H_2O$, addition of 1.00 mole of $H_2O$ in the calculation to reflect $Gd^{3+}$ bound $H_2O$ gives the following closely consistent calculated values: C, 44.87%; H, 5.94%; N, 8.21%. Minor Conformer: Calc'd. for $C_{32}H_{47}N_5O_9GdNa \cdot 4.75 H_2O$: C, 42.28; H, 6.26; N, 7.70. Found: C, 42.42; H, 6.19; N, 7.27.

The minor conformer is particularly preferred as it has been found to have exceptionally high levels of uptake in the liver.

EXAMPLE 5

10-[2-[(Carboxymethyl)(3,5-di-(1,1-dimethylethyl) phenyl)amino]-2-oxoethyl]-1,4,7,10-tetraazacyclododecane-1,4,7-triacetic acid ("3,5-BPA-DO3A")

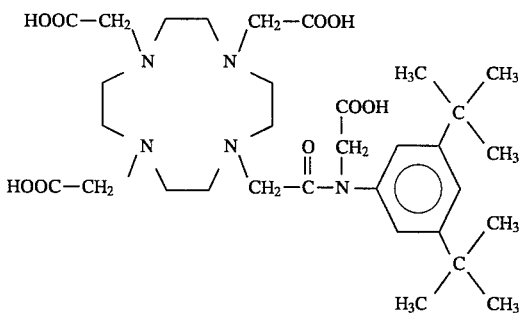

The title compound was prepared using the methodology of Example 3 (Schemes A and D), except that 3,5-di(1,1-dimethylethyl)aniline was employed in place of 4-aminobiphenyl.

Microanalysis calc'd $C_{32}H_{51}N_5O_9 \cdot 1.65H_2O$: C, 56.56; H, 8.05; N, 10.31; O, 25.08; Found: C, 56.37; H, 8.31; N, 10.19; O, 25.13.

EXAMPLE 5A

10-[2-N-(3,5-Di-tert-butylphenyl)-N-(carboxymethyl) amino]-2-oxoethyl]-1,4,7,10-tetraazacyclododecanatogadolinium ("Gd-3,5-BPA-DO3A")

A flask was charged with the product of Example 5 (0.500 g), 50% aqueous $CH_3OH$ (32 mL) and $Gd(OAc)_3$ (0.571 g in 5 mL water) (Ac=acetate). The pH of the mixture was 4.04. The mixture was stirred at 60° C. for 4.5 hours. The resulting solution was cooled to room temperature and the $CH_3OH$ was removed by rotary evaporation. The product was purified by preparative reverse phase chromatography on CHP-20 resin to provide the title product as a white foam.

Microanalysis calc'd $C_{32}H_{48}N_5O_9Gd \cdot 2.93H_2O$: C, 44.86; H, 6.34; N, 8.17; O, 22.28; Gd, 18.35%; Found: C, 45.01; H, 5.97; N, 8.02; $H_2O$, 6.14%.

EXAMPLE 6

10-[2-[(Carboxymethyl)[4-(cyclohexyl)phenyl] amino]-2-oxoethyl]-1,4,7,10-tetraazacyclododecane-1,4,7-triacetic acid ("CPA-DO3A")

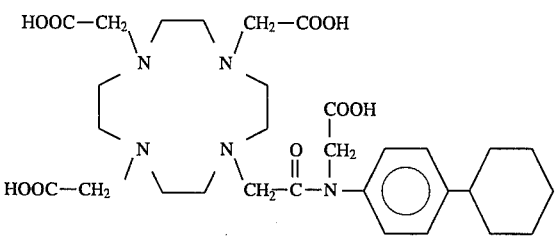

The title compound was prepared using the methodology of Example 2 (Schemes B and D), but substituting 4-cyclohexylaniline for 4-tert-butylaniline.

Microanalysis calc'd for $C_{30}H_{45}N_5O_9$: C, 58.14; H, 7.32; N, 11.30; O, 23.24; Found: C, 52.83; H, 7.53; N, 10.08; $H_2O$, 4.46.

EXAMPLE 6A

10-[2-N-(4-Cyclohexyl)phenyl]-N-(carboxymethyl) amino]-2-oxoethyl]-1,4,7,10-tetraazacyclododecanato-1,4,7-triacetic acid monogadolinium, monosodium salt ("Gd-CPA-DO3A")

To a solution of 30.0 g of the title compound of Example 6 in 750 mL of water was added 23.7 g of gadolinium triacetate tetrahydrate. The mixture was stirred at 60° C. for 6 hours. The pH of the solution was then adjusted to 8.0 by adding aqueous sodium hydroxide solution. The insoluble material was filtered and the volume of the solution was reduced to 500 mL by concentration.

The product was purified by reverse phase column chromatography using a water-ethanol gradient elution. The product-containing fractions were pooled and the volatiles was removed. The resulting solid was dried under high vacuum to give 35.77 g (92.7% yield) of the title product as a white foam.

Mass Spectrum: 775 (M+H)⁺, 797(M+Na)⁺, 819(M+2Na—H)⁺ Microanalysis: Calc'd for $C_{30}H_{41}N_5O_9NaGd \cdot 4H_2O$: C, 40.87; H, 5.78; N, 7.94; O, 25.02 Gd, 17.82; Na, 2.61. Found: C, 40.86; H, 5.84; N, 7.91.

EXAMPLE 6B

10-[2-N-(4-Cyclohexylphenyl)-N-(carboxymethyl) amino]-2-oxoethyl]-1,4,7,10-tetraazacyclododecane triacetic acid monogadolinium N-methylglucamine salt ("Gd(CPA-DO3A)⁻ (NMGH)⁺")

The title compound of Example 6 was also chelated with gadolinium in the form of the N-methylglucamine salt as follows. 1.637 g of the acid-form of the title compound of Example 6 was dissolved in 50 mL water. To this 0.5 g (10% excess) $Gd_2O_3$ was added and the reaction mixture was heated at 80° C. for 18 h. 0.488 g NMG (N-methylglucamine) (2.5 mmol) was added as a solid. The resulting precipitate was removed by centrifugation. The removal of water by rotory evaporation gave a syrup. Addition of ethanol gave a white solid, which was separated and dried under vacuum at 80° C. This afforded the title product as a solid (1.29 g, 53.3% yield).

Mass spectrum (FAB+): m/Z 775 (M+H)$^+$, 797 (M+Na+H)$^+$. Microanalysis: Calculated for $C_{37}H_{59}N_6O_{14}Gd\cdot 7.0 H_2O$: C, 40.54; H, 6.66; N; 7.67. Found: C, 40.76; H, 6.27; N, 7.39.

EXAMPLE 7

10-[2-[(Carboxymethyl)(4-n-decylphenyl)amino]-2-oxoethyl]-1,4,7,10-tetraazacyclododecane-1,4,7-triacetic acid ("DPA-DO3A")

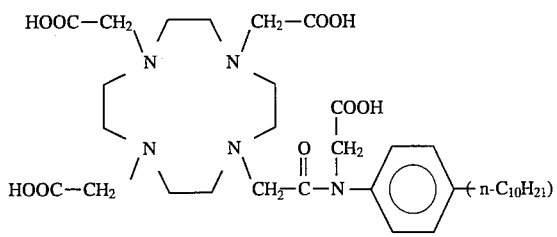

The title compound was prepared using the methodology of Example 3 (Schemes A and D) except that 4-decylaniline was employed in place of 4-aminobiphenyl.

Microanalysis calc'd for $C_{34}H_{55}N_5O_9\cdot 0.31\ H_2O$: C, 59.75; H, 8.20; N, 10.25; O, 21.80; Found: C, 59.37; H, 8.53; N, 10.02.

EXAMPLE 7A

10-[2-[(Carboxymethyl)(4-n-decylphenyl)amino]-2-oxoethyl]-1,4,7,10-tetraazacyclododecane-1,4,7-triacetic acid monogadolinium monosodium salt ("Gd-DPA-DO3A")

The synthesis of the title chelate was achieved by the method of Example 3A, but starting with the compound of Example 7. 40.74 mg of the Example 7 ligand and 6.0 mL of 9.93 mM GdCl$_3$ solution were used for this synthesis. The title chelate was recovered as a solid material (37 mg, 73.6% yield).

Mass spectrum (FAB+): m/Z: 833(M+H)$^+$ and 855 (M+Na)$^+$. Microanalysis: Calc'd for $C_{34}H_{51}O_9GdNa\cdot 0.97\ H_2O$: C, 46.86; H, 6.12; N; 8.05. Found: C, 46.71; H, 6.18; N; 8.05.

EXAMPLE 8

10-[2-[[3,5-Bis[[(2-methylbutyl)amino]carbonyl-phenyl]-(carboxymethyl)amino]-2-oxoethyl]-1,4,7,10-tetraazacyclododecane-1,4,7-triacetic acid, triethylamine (1:2) salt ("CAA-DO3A")

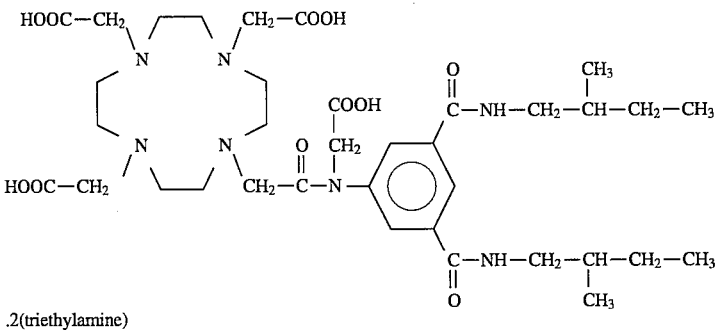

A. N,N'-Bis[(2-methylbutyl)amino]-5-nitro-1,3-benzenedicarboxamide

To a solution of dimethyl-5-nitro-isophthalate (14.0 g) in methanol was added 2-methylbutylamine (12.5 g), and the mixture was kept at reflux for 48 hours. Methanol was removed in vacuo, and the residue was dissolved in ethyl acetate (200 mL) and washed sequentially with 10% hydrochloric acid (200 mL), 10% aqueous sodium bicarbonate solution (20 mL) and water (100 mL). The ethyl acetate layer was dried; removal of the solvent afforded the title compound. Recrystallization from ethyl acetate and hexane gave the nitrobisamide (title A compound) as colorless needles (19.6 g, yield 96%). m.p.: 147°–148° C. (uncorrected).

Elemental Analysis: Calcd. for $C_{18}H_{29}N_3O_2$: C, 67.68; H, 9.15; N, 13.15. Found: C, 68.07; H, 9.30; N, 13.26.

B. 5-Amino-N,N'-bis[(2-methylbutyl)amino]-1,3-benzenedicarboxamide

A solution of the title A nitrobisamide (17.45 g) in methanol (180 mL) was hydrogenated over 10% palladium on carbon (500 mg) for a period of 3 hours. The catalyst was filtered off and the solvent was removed in vacuo to afford the title B compound as a colorless solid. This was crystallized from acetone/hexane to afford the title B aminobisamide as colorless needles (15.8 g, yield 98%). m.p.: 162°–163° C. (uncorrected).

Elemental Analysis: Calcd. for $C_{18}H_{29}N_3O_2$: C, 67.68; H, 9.15; N, 13.15 Found: C, 67.96; H, 9.27; N, 13.03.

C. N,N'-Bis(2-methylbutyl)-5-[[(phenylmethoxy)carbonyl]amino]-1,3-benzenedicarboxamide To a cooled solution of the title B compound (15.4 g) in anhydrous dimethylacetamide (DMA) (75 mL) at 0° C. was added benzyl chloroformate (Aldrich, 9.4 g). The clear solution was stirred at 0° C. for 2 hours. DMA was removed in vacuo. The residue was dissolved in EtOAc (150 mL), and was washed with aqueous NaHCO$_3$ solution (30 mL) and with H$_2$O (2×50 mL). The organic layer was dried over anhydrous MgSO$_4$ and the solvent was removed to obtain the crude product as an oily liquid. Recrystallization of the crude material from EtOAc/hexanes (5/1) afforded the title C compound as a white solid (17.0 g, 81.6%). m.p.: 130.5°–132.5° C. (uncorrected).

Elemental Analysis: Calcd. for $C_{26}H_{35}N_3O_4$: C, 68.85; H, 7.78; N, 9.26; O, 14.11 Found: C, 68.64; H,7.91; N, 9.20.

D. N-[3,5-Bis[[(2-methylbutyl)amino]carbonyl]phenyl-N-[(phenylmethoxy)carbonyl]glycine-1,1-dimethylethyl ester To a suspension of NaH (0.4 g) in anhydrous tetrahydrofuran (THF) (50 mL) was added a solution of the title C compound (6.8 g) in THF (150 mL) and the mixture was stirred for 1 hour. t-Butyl bromoacetate (3.6 g) was added to the reaction mixture and stirring was continued for 24 hours. The excess of NaH was carefully decomposed by the addition of water (4 mL). The volatiles were removed in vacuo and the residue was dissolved in ethyl acetate (200 mL), washed with water (3×100 mL) and dried. The volatiles were removed to afford the crude product which was recrystallized from ethyl acetate and hexane to afford the title D compound as colorless crystals (6.75 g, yield 79.3%). m.p.: 141°–142° C. (uncorrected).

Elemental Analysis: Calcd. for $C_{32}H_{45}N_3O_6$: C, 67.70; H, 7.99; N, 7.40 Found: C, 67.82; H, 8.12; N, 7.54.

E. N-[3,5-Bis[[(2-methylbutyl)amino]carbonyl]phenyl]glycine, 1,1-dimethylethyl ester To a solution of the title D compound (6.3 g) in methanol (100 mL) was added 1,4-cyclohexadiene (20 mL) and Pd/C (10%, 2.0 g) and the mixture was refluxed for 2 hours. The catalyst was filtered off and the solvent was removed to give the crude product. Recrystallization from ethyl acetate and hexane afforded the title E compound as colorless needles (4.75 g, 98%). m.p.: 80°–82° C. (uncorrected).

Elemental Analysis: Calcd. for $C_{24}H_{39}N_3O_4$: C, 66.30; H, 9.07; N, 9.76 Found: C, 66.25; H, 8.92; N, 9.72.

F. N-[3,5-Bis[[(2-methylbutyl)amino]carbonyl]phenyl]-N-(chloroacetyl)glycine, 1,1-dimethylethyl ester To a solution of the title E compound (4.7 g) in DMA (40 mL) was added chloroacetyl chloride (3.05 g) and the mixture was stirred for 4 hours. DMA was removed under vacuum, and the residue was dissolved in ethyl acetate (200 mL), and washed successively with water (100 mL), aqueous sodium carbonate (100 mL) and saturated sodium chloride (100 mL). The organic layer was dried and solvent removal afforded the crude chloroacetyl derivative. This was crystallized from ethyl acetate and hexane to afford the pure title F compound as white crystals (4.4 g, yield 85%). m.p.: 159°–160° C. (uncorrected).

Elemental Analysis: Calcd. for $C_{26}H_{40}N_3ClO_5$: C, 61.22; H, 7.90; N, 8.24; Cl, 6.95 Found: C, 61.42; H, 8.15; N, 8.33; Cl, 7.23.

G. 10-[2-[[3,5-Bis[[(2-methylbutyl)amino]carbonylphenyl](carboxymethyl)-amino-2-oxoethyl]-1,4,7,10-tetraazacyclododecane-1,4,7-triacetic acid, triethylamine (1:2) salt To a solution of 1,4,7,10-tetrazacyclododecane-1,4,7-triacetic acid-tris(1,1-dimethylbutyl)ester (prepared in Example 3 above) (4.112 g) in anhydrous acetonitrile (20 mL) was added potassium carbonate (4.4 g), sodium iodide and the title F compound (4.08 g). The mixture was heated at 60° C. for 5 hours. The mixture was then stirred at room temperature for 18 hours, the inorganic salts were filtered off, and the solvent was removed in vacuo.

The resulting glassy solid was dissolved in ethyl acetate (150 mL), and the organic layer was washed with water (2×100 mL) and dried. Evaporation of volatiles afforded the crude tetra butyl ester of the title compound. This was dissolved in trifluoroacetic acid (TFA) (250 mL) and treated with anisole (25 mL) for 4 hours at room temperature. TFA was removed under vacuum, and the residue was dissolved in water (400 mL). The aqueous solution was washed with ether (300 mL). The pH of the aqueous solution was adjusted to 10 with 5M NaOH solution and this was treated with decolorizing charcoal for 1 hour at 80° C. The charcoal was filtered off, the aqueous layer was diluted to 2 L and applied onto a Sephadex G-25 column (2 L). The column was washed with 5 mM tetraethyl ammonium bicarbonate solution (2 L) and the column was eluted with a gradient consisting of 8 L of 5 mM and 8 L of 0.5M aqueous triethyl ammonium bicarbonate. Fractions containing the desired product were combined and solvent removal afforded the pure title G salt (1.67 g, yield 42%).

Elemental Analysis: Calcd. for $C_{48}H_{87}N_9O_{11}\cdot 0.95\ H_2O$: C, 58.62; H, 9.11; N, 12.82 Found: C, 58.68; H, 9.30; N, 12.76.

EXAMPLE 8A

10-[2-[[3,5-Bis[[(2-methylbutyl)amino]carbonylphenyl]-carboxymethyl)-amino-2-oxoethyl]-1,4,7,10-tetraazacyclododecane-1,4,7-triacetic acid monogadolinium salt, ("Gd-CAA-DQ3A")

A 10 mL round bottomed flask was charged with the title compound of Example 8 (500 mg) and distilled deionized water (5.0 mL) and the mixture was stirred. The pH of the mixture was adjusted to 4.5 with dilute acetic acid. Then a solution of gadolinium acetate tetrahydrate (305 mg) in 7.5 mL of distilled, deionized water was added. The mixture was stirred at 45° C. for 18 hours. The crude material was purified by reverse phase column chromatography using a water-ethanol gradient elution. The volatiles were removed by lyophilization to give 418 mg (91.1%) of the title product as a white powder.

Mass Spectrum (FAB+): m/z at 916 to 921 $(M-H)^+$ and 938 to 943 $(M+Na)^+$, 960 to 965 $(M+2Na)^+$. Microanalysis: Calculated for $C_{36}H_{53}N_7O_{11}GdNa\cdot 2.92\ H_2O$: C, 43.55; H, 5.97; N, 9.88. Found: C, 43.60; H, 6.21; N, 9.83.

EXAMPLE 9

10-[2-[N-(4-Cyclohexylphenyl)-N-(3-amino-2-oxoethyl)amino]-2-oxoethyl]-1,4,7,10-tetraazacyclododecane-1,4,7-triacetic acid ("ACPA-DO3A")

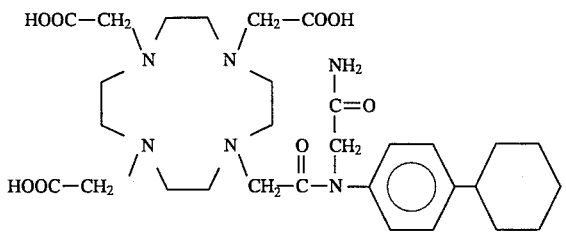

The title compound was prepared using the procedure of Example 3 (Schemes A and D), but substituting α-iodoacetamide for tert-butylbromoacetate.

Microanalysis calc'd for $C_{30}H_{46}N_6O_8\cdot 1.15\ H_2O$: C, 56.35; H, 7.61; N, 13.14; O, 22.89; Found: C, 56.50; H, 7.75; N, 13.15.

EXAMPLE 9A

10-[2-[(2-Amino-2-oxoethyl)(4-cyclohexylphenyl)amino]-2-oxoethyl]-1,4,7,10-tetraazacyclododecane-1,4,7-triacetic acid monogadolinium monosodium salt ("Gd-ACPA-DO3A")

The synthesis of the title chelate was achieved by the method of Example 3A, but starting with the compound of Example 9. 60.17 mg of the Example 9 ligand and 10.0 mL of 9.934 mM GdCl₃ solution were used for this synthesis. The title chelate was recovered as a solid material (37 mg, 75% yield).

Mass spectrum (FAB+): m/Z: 774 (M+H)⁺. Microanalysis: Calc'd for $C_{30}H_{43}N_6O_8Gd \cdot 0.92\ H_2O$: C, 45.64; H, 5.72; N, 10.64. Found: C, 45.23; H, 5.94; N, 10.48.

EXAMPLE 10

10-[2-[N-(4-Cyclohexylphenyl)-N-[2-(N-carboxymethyl)aminoethyl]amino]-2-oxoethyl]-1,4,7,10-tetraazacyclododecane-1,4,7-triacetic acid ("ZCPA-DO3A")

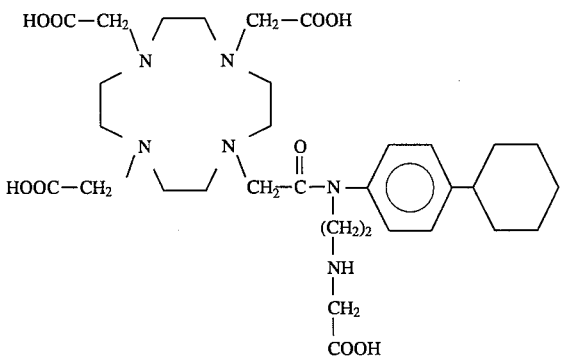

A. 2-Chloroethyl-N-(4-cyclohexyl)phenyl-carbamate

To a solution of 4-cyclohexylaniline (35.6 g) in dimethylacetamide (500 mL) was added with stirring dropwise 2-chloroethyl chloroformate (31.5 g) at 0° C. during 5 minutes. The mixture was stirred at room temperature for 2.5 hours and then the solvent was removed in vacuo. The residue was dissolved in methylene chloride and the organic layer was washed with a mixture of equal volumes of brine and saturated aqueous sodium bicarbonate. The organic layer was separated and the aqueous layer was back-extracted with methylene chloride. The combined organic layers were washed with brine and dried (Na₂SO₄). Evaporation gave an off-white solid (56.8 g). Crystallization from ethyl acetate-hexane furnished the title A compound (35.3 g) as a white crystalline solid. m.p. 102°–103° C.

B. N-(2-Hydroxyethyl)-4-cyclohexylaniline

To a solution of the title A compound (30.0 g) in absolute ethanol (425 mL) was added at 60° C. a solution of potassium hydroxide (34.1 g, 87%, 0.53 mol) in absolute ethanol (850 mL) and the mixture was refluxed for 15 hours under nitrogen. Water (60 mL) was added and the mixture was kept at reflux for an additional 4 hours. The mixture was concentrated and the residual solution was diluted with water (400 mL) and methylene chloride (400 mL). The pH of the aqueous layer was adjusted to 10.0 using acetic acid. The layers were separated and the aqueous layer was back extracted with methylene chloride. The combined organic layers were washed with water and brine and then dried (Na₂SO₄). Evaporation afforded the title B compound (23.2 g) as a yellow solid, m.p. 39°–41° C.

C. N-(2-Bromoethyl)-4-cyclohexylanilinium bromide

A solution of the title B compound (11.5 g, 52 mmol) in 48% hydrobromic acid (35 mL) was boiled and the distillate was collected until the bath temperature reached 190° C. The total volume of distillate was 31.5 mL. The residual solid was crystallized from absolute ethanol to give the title C compound (12.7 g) as a tan colored solid, m.p. 177°–178° C.

D. t-Butyl N-benzyl-N-2-[[N-(4-cyclohexyl)phenyl]amino]ethyl-glycinate

A flask was charged with the title C compound (10.89 g), acetonitrile (45 mL), diisopropylethylamine (9.69 g) and t-butyl N-benzylglycinate (6.64 g, prepared as described by A. Padwa et al., *J. Org. Chem.*, 1985, 50, 4006–14). The mixture was heated to reflux under nitrogen for 6 hours. The volatiles were removed in vacuo and a solution of the residue in methylene chloride was washed with aqueous 15% potassium carbonate. Drying of the organic layer (Na₂SO₄), followed by solvent removal gave a red solid, which was flash chromatographed over silica gel to obtain the title D compound (3.92 g).

Microanalysis calc'd for $C_{27}H_{38}N_2O_2$: C, 76.74; H, 9.06; N, 6.63; Found: C, 76.54; H, 8.83; N, 6.72.

E. t-Butyl N-benzyl-N-2-[[N-2-chloro-1-oxo-ethyl-N-(4-cyclohexyl)phenyl]amino]ethyl-glycinate A flask was charged with the title D compound (3.58 g, 8.5 mmol) and dimethylacetamide (15 mL). The mixture was cooled to 0° C. and chloroacetyl chloride (1.8 g, 16 mmol) was added dropwise with stirring over 1 minute. The mixture was stirred at 0° C. for 15 minutes and then at room temperature for 1.5 hours. The volatiles were removed in vacuo to give a residue which was dissolved in methylene chloride and washed with aqueous 5% potassium bicarbonate. The aqueous layer was back extracted with methylene chloride. The combined organic layers were washed with aqueous 5% potassium bicarbonate and then dried (brine, Na₂SO₄). Evaporation of volatiles gave a crude oil. Flash chromatography over silica gel using ethyl acetate-hexane furnished the title E compound (3.52 g) as a pale yellow solid. TLC $R_f$ [Ethyl acetate-hexane (2:5) over silica gel] :0.41.

Microanalysis calc'd for $C_{29}H_{39}N_2O_3Cl$: C, 69.79; H, 7.88; N, 5.61; Cl, 7.10; Found: C, 69.43; H, 8.11; N, 5.73; Cl, 7.22.

F. 10-[2-[N-(4-Cyclohexylphenyl)-N-[2-(N-benzyl-N-carboxymethyl)aminoethyl]-amino]-2-oxoethyl]-1,4,7,10-tetraazacyclododecane-1,4,7-triacetic acid tetra-t-butyl ester The title E compound (3.08 g, 6.2 mmol) in acetonitrile (15 mL) was treated with 1,4,7,10-tetraazacyclododecane-1,4,7-triacetic acid-tris(1,1-dimethylethyl) ester (prepared in Example 3) (3.1 g), potassium carbonate (2.1 g), and sodium iodide (0.93 g). The mixture was stirred at 60° C. for 15 hours. Acetonitrile (85 mL) was added and the mixture filtered through Celite 521. Evaporation of the solvent furnished a yellow foam, which was flash chromatographed over silica gel. This gave the title F compound (3.6 g) as a pale yellow foam.

Microanalysis calc'd for $C_{55}H_{88}N_6O_9$: C, 67.59; H, 9.08; N, 8.60; O, 14.73; Found: C, 58.15; H, 7.93; N, 7.52.

The analysis reflects the presence of complexed alkali metal salts.

G. 10-[2-(N-(4-Cyclohexylphenyl)-N-(2-(N-benzyl-N-carboxymethyl)aminoethyl)-amino]-2-oxoethyl]-1,4,7,10-tetraazacyclododecane-1,4,7-triacetic acid A solution of the title F compound (3.06 g) in a mixture of trifluoroacetic acid (150 mL) and anisole (18 mL) was stirred at room temperature for 4.75 hours. The volatiles were removed in vacuo and water (100 mL) containing sodium bisulfite (100 mg) was added. Water was removed in vacuo and this process was repeated once more to give a pale yellow foam. Desalting was accomplished by ion exchange chromatography which furnished the bis-ammonium salt of the crude product (1.6 g) along with impurities. Anion exchange chromatographic purification furnished the title G compound as a formic acid salt (1.1 g).

Microanalysis calc'd for $C_{39}H_{56}N_6O_9 \cdot HCOOH$: C, 59.92; H, 7.33; N, 10.48; Found: C, 59.80; H, 7.48; N, 10.40.

H. 10-[2-[N-(4-Cyclohexylphenyl)-N-[2-(N-carboxymethyl)aminoethyl]amino]-2-oxoethyl]-1,4,7,10-tetraazacyclododecane-1,4,7-triacetic acid Catalytic hydrogenolysis of the title G compound (0.92 g) in the presence of 10% Pd/C (0.3 g) in acetic acid (25 mL) at a hydrogen pressure of 55 psi was carried out for 32 hours at room temperature. The catalyst was filtered off and the solvent removed in vacuo. Water (60 mL) and acetic acid (10 mL) were added to the residue and the solution was filtered again through a 0.2μ filter. The volatiles were removed in vacuo. Water was added and removed in vacuo and this process was repeated twice. A solution of the residue in water was lyophilized to obtain the title H compound (0.7 g).

Microanalysis calc'd for $C_{32}H_{50}N_6O_9 \cdot 4.12H_2O$: C, 52.15; H, 7.96; N, 11.40; Found: C, 52.68; H, 8.17; N, 11.41.

EXAMPLE 10A

10-[2-[N-(4-Cyclohexylphenyl)-N-(2-(2-carboxymethyl)aminoethyl)-amino]-2-oxoethyl] 1,4,7,10-tetraazacyclododecane-1,4,7-triacetic acid monogadolinium monosodium salt ("Gd-ZCPA-DO3A")

7.0 mL of 9.17 mM $GdCl_3$ was mixed with 39.3 mg of the title compound of Example 10. The method of synthesis and purification employed was the same as that used in preparing the chelate of Example 3A. The title chelate was recovered at the end of the reaction as a solid material (36 mg, 69% yield). Mass spectrum (FAB+): m/Z: 818 $(M+H)^+$ and 840 $(M+Na)^+$.

Microanalysis: Calc'd for $C_{32}H_{47}N_6O_9GdNa \cdot 1.5 H_2O$: C, 44.33; H, 5.80; and N, 9.69. Found: C, 4.14; H, 6.28; N, 9.49.

EXAMPLE 11

10-[2-[N-(4-Cyclohexylphenyl)-N-[(2-sulfonyloxyethyl)amino-2-oxoethyl]amino]-2-oxoethyl]-1,4,7,10-tetraazacyclododecane-1,4,7-triacetic acid, gadolinium chelate ("Gd-TCPA-DO3A")

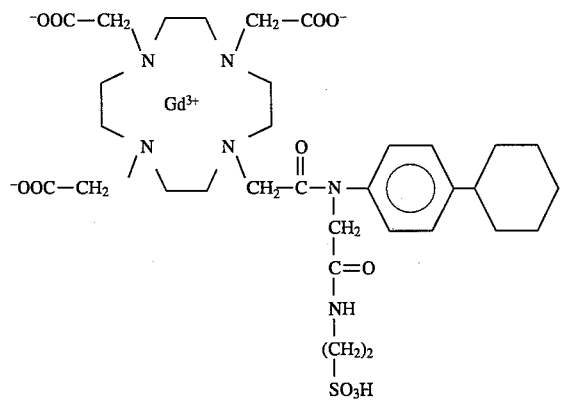

Taurine (376 mg) and triethylamine (0.5 mL) were added to a stirred solution of the title compound of Example 6A (2.00 g) and N-ethoxycarbonyl-2-ethoxy-1,2-dihydroquinoline ("EEDQ") (869 mg) in 5 mL of dry dimethylformamide ("DMF"). The resulting suspension was heated at 90° C. under nitrogen until the solution clarified (~20 min.).

The solution was stirred at 90° C. for 4 hours. The solution was then cooled to room temperature with stirring and was poured slowly into 50 mL of stirred, chilled anhydrous diethyl ether in an ice bath for 1 hour and was kept in the refrigerator overnight. The resulting heavy precipitate was filtered and this was washed with ether (4×20 mL). The collected solid was then air-dried to obtain the presumed triethylammonium salt of the title compound.

The resulting salt was dissolved in 42 mL of 0.2N methanolic NaOH. The solution was then diluted with 160 mL of ether and the solution was stirred 3 hours at 0° C. A heavy precipitate formed and this was collected and washed with methanol-ether (1/3 V/V; 2×30 mL), ether (5×20 mL) and air-dried. This provided a crude product (2.00 g, 88.1% yield).

This crude product was dissolved in ~60 mL of distilled, deionized water and was applied to a 550 mL column of CHP-20 resin. The column was eluted with water (16×75 mL, 5×250 mL), 0.05M $CH_3COOH$ in water (17×75 mL), 0.05M $CH_3COOH$ in 5% aqueous $C_2H_5OH$ (16×75 mL), 0.05M $CH_3COOH$ in 10% aqueous $C_2H_5OH$ (19×75 mL), 0.05M $CH_3COOH$ in 25% aqueous $C_2H_5OH$ (21×75 mL), 0.05M $CH_3COOH$ in 30% aqueous $C_2H_5OH$ (20×75 mL), 0.05M $CH_3COOH$ in 50% aqueous $C_2H_5OH$ (20×75 mL), 0.05M $CH_3COOH$ in 80% aqueous $C_2H_5OH$ (3×250 mL) and then distilled, deionized water (2000 mL). A total of 150×75 mL and 16×250 mL fractions were collected. The compound eluted in fractions 82 to 118. Fractions 83 to 116 were pooled and the volatiles were removed by rotary evaporation. The remaining acetic acid was removed by coevaporation with water (3×100 mL). This provided 1.7 g (85% recovery from the column, 74% yield overall) of the title product as a very light blue glassy solid.

A second CHP-20 column was used to further purify the compound. The product from the first column was dissolved in 50 mL of distilled, deionized water, and was applied to a 550 mL CHP-20 column. The column was washed with water (2×150 mL, 10×50 mL), and then ethanol/water mixtures as follows: 1% $C_2H_5OH$ (14×50 mL), 5% $C_2H_5OH$ (12×50 mL), 10% $C_2H_5OH$ (17×50 mL), 20% $C_2H_5OH$ (17×50 mL), 30% $C_2H_5OH$ (24×50 mL), 50% $C_2H_5OH$ (20×50 mL), 75% $C_2H_5OH$ (3×250 mL) and water. A total of 130 fractions was collected. The title compound eluted in fractions 78 to 97. Fractions 79 to 93 were collected and the volatiles were removed by rotary evaporation. Residual ethanol was removed by coevaporation with distilled, deionized water (2×60 mL). The resulting material was dried under high vacuum for 2 days; this gave 1.51 g (88% yield from last column) of the title product as a very light blue glassy solid.

HPLC: Major Component: Ret. time: 7.57 min. (>95.8% based on the area percent) Column: ET 250/1/4"4.6 Nucleosil 120-5, C-18, Mobile phase: 25% of $CH_3CN$ in 50 mM TrisOAc (aq) and 10 mM $Na_2EDTA$ (aq), pH 7.0; Flow rate: 1.0 mL/min. Detection: UV @ 254 nm.

Microanalysis: $C_{32}H_{46}N_6O_{11}SGd \cdot 2.20H_2O$ Calc: C, 41.75; H, 5.63; N, 9.13; S, 3.48; Gd, 17.08; O, 22.94 Found: C, 41.69; H, 6.01; N, 9.06; S, 3.26.

EXAMPLE 12

10,10'-[[[[1,2-Ethanediylbis[(carboxy-methyl)nitrilo]]-bis(2-oxo-2,1-ethanediyl)bis[(4-cyclohexyl)phenyl) nitrilo]]bis(2-oxo-2,1-ethanediyl)bis[1,4,7,10-tetraazacyclododecane-1,4,7-triacetic acid]("DAD-DO3A")

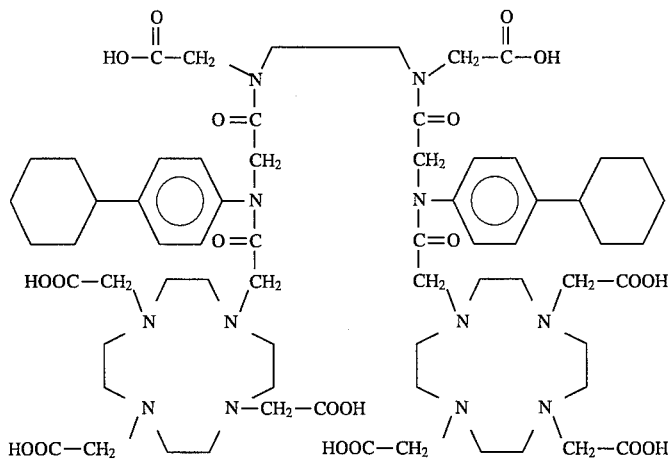

A. N,N'-(1,2-Ethanediyl)bisglycine,bis(1,1-dimethylethyl) ester tert-Butylbromoacetate (2.60 g) was added dropwise with stirring over a 20 minute period to a cooled solution of dimethylformamide (20 mL) and ethylenediamine (1.05 g). Stirring was continued for 5 hours at 5° C. followed by 1 hour at ambient temperature. The solvent was removed in vacuo at 35° C. and the resulting oily residue was re-dissolved in CHCl₃ (75 mL). The organic phase was washed with saturated NaHCO₃ (50 mL), water (50 mL) and saturated aq. NaCl (50 mL) before concentration in vacuo to a clear colorless oil (1.02 g). The crude title A material was used without further purification.

Mass spectrum: (CI, NH₃/Dep) m/e 289⁺ (M+H)⁺.

B. N,N'-(1,2-Ethanediyl)bis[N-(chloroacetyl)glycine], bis(1,1-dimethylethyl) ester Into a 100 mL three-necked flask, equipped with two liquid addition funnels and a stir bar, was placed the title A compound (1.02 g) dissolved in CHCl₃ (8 mL). The addition funnels were charged with chloroacetyl chloride (1.19 g) in CHCl₃ (7 mL) and K₂CO₃ (1.07 g) in water (7 mL) respectively. The contents of both addition funnels were added dropwise over a one hour period to the cooled (5° C.) stirring bis-ester solution. Upon complete addition, stirring was continued at 5° C. for 2 hours and then at room temperature for an additional 1 hour. The organic (CHCl₃) layer of the biphasic reaction mixture was separated and washed with small portions of water (2×10 mL) and saturated NaCl (10 mL). The organic layer was dried (MgSO₄), filtered and concentrated in vacuo to a viscous oil (1.7 g). The crude title B product was purified by flash column chromatography over silica gel (eluted with 1:1 ethyl acetate/hexanes) to yield 1.0 g (65%) of a clear colorless oil which solidified upon standing. TLC: R_f=0.75 (silica gel, ethyl acetate/hexanes 65:35, UV detection).

Microanalysis: Calculated for $C_{18}H_{30}N_2Cl_2O_6 \cdot 0.15 H_2O$: C, 48.69; H, 6.88; N, 6.31; Cl, 15.97; O, 22.15%. Found: C, 49.00; H, 6.94; N, 6.00; Cl, 15.57%.

C. N,N'-(1,2-Ethanediyl)bis[N-[N-(4-cyclohexylphenyl)glycyl]glycine], bis(1,1-dimethylethyl)ester Cyclohexylaniline (0.48 g), sodium iodide (0.46 g) and potassium carbonate (0.52 g) were combined in acetonitrile (3 mL). To this stirred solution at room temperature was added the title B chloroamide (0.55 g) in acetonitrile (3 mL) dropwise over a 45 minute period. The reaction was stirred at room temperature for 19 hours. The solid which had formed was removed by filtration. The solid was collected, re-dissolved in CH₂Cl₂ (75 mL) and washed with water (2×25 mL), 1% aqueous sodium thiosulfate (1×25 mL) and saturated aqueous NaCl (1×25 mL) respectively. The organic layer was dried (MgSO₄), filtered and the solvent was removed in vacuo leaving the title C compound as a pale yellow foam (0.55 g).

Mass spectrum: (CI, NH₃) m/e 719⁺ (M+H)⁺; 717⁻ (M-H)⁻; 569⁻ (M-H-2 tert-butanol); 643⁻(M-H-tert-butanol).

D. N,N'-(1,2-Ethanediyl)bis[N-(N-(chloroacetyl)-N-(4-cyclohexylphenyl)glycyl]glycine], bis(1,1-dimethylethyl) ester The title C bis-cyclohexyldiamide (0.45 g, 0.63 mmol) was dissolved in anhydrous dimethylacetamide ("DMA") (15 mL) and cooled to 0°–5° C. Chloroacetyl chloride (0.21 g, 1.90 mmol) was added dropwise over a 10 minute period. Stirring was continued for 1 hour at 0°–5° C. and then at room temperature for 2.5 hours. Upon completion of the reaction the solvent was removed in vacuo at 45° C. leaving a yellow oil. The crude product was redissolved in ethyl acetate (80 mL) and washed successively with water (2×30 mL), 10% aqueous sodium bicarbonate (30 mL) and saturated aqueous NaCl (30 mL). The organic phase was dried (MgSO₄) and filtered, the solvent was removed in vacuo leaving 0.52 g (95%) of a white foam. This was further purified by flash column chromatography over silica gel giving 0.48 g (88% overall) of the title D compound as a white solid. m.p.: 106°–108° C.

Microanalysis: Calculated for $C_{46}H_{64}N_4Cl_2O_8 \cdot 0.13 H_2O$: C, 63.20; H, 7.41; N, 6.22; Cl, 8.11; O, 14.87%. Found: C, 63.29; H, 7.45; N, 6.22; Cl, 8.02; H₂O, 0.26%.

E. 10,10'-[[[[1,2-Ethanediyl]]bis[[2-(1,1-dimethylethoxy-2-oxoethyl]nitrilo]]bis(2-oxo-2,1-ethandiyl)]bis[(4-cyclohexylphenyl)nitrilo]]bis(2-oxo-2,1-ethanediyl)]bis[1,4,7,10-tetraazacyclododecane-1,4,7-triacetic acid, hexakis (1,1-dimethylethyl)ester 1,4,7,10-Tetraazacyclododecane-1,4,7-triacetic acid, tris(1,1-dimethylethyl)ester hydrochloride (prepared in Example 3C) (0.56 g) was added to a 50 mL round-bottomed flask containing anhydrous DMF (6 mL) and powdered potassium carbonate (0.56 g). The suspension was stirred at room temperature for 45 minutes. Sodium iodide (0.15 g) was added; the reaction mixture was warmed to 60° C. with stirring and the title D tetraamide (0.41 g) in DMF (2 mL) was added dropwise over a 1 hour period. The mixture was stirred for 24 hours at 55° C. and 48 hours at ambient temperature. The reaction mixture was concentrated in vacuo and the residue was partitioned between CH₂Cl₂ (80 mL) and water (35 mL). The organic layer was separated and washed with water (35 mL) and saturated aqueous sodium chloride (35 mL). The organic layer was further dried ($Na_2SO_4$) and filtered. The solvent was removed in vacuo to give 0.94 g (100%) of the title E compound as an off-white solid.

Mass spectrum: (FAB) m/e $1850.1^+$ $(M+Na)^+$; $2001.1^+$ $(M+Na+NaI)^+$.

10,10'-[[[[1,2-Ethanediyl]bis[(carboxymethyl)nitrilo]]bis(2-oxo-2,1-ethanediyl)bis[(4-cyclohexylphenyl)nitrilo]]bis(2-oxo-2,1-ethanediyl)bis[1,4,7,10-tetraazacyclododecane-1,4,7-triacetic acid]

The title E octa-tert-butylester (0.94 g) was dissolved in 200 mL of trifluoroacetic acid/anisole (9/1 v/v). The pale yellow solution was stirred at room temperature for 24 hours. Removal of the solvent in vacuo at 50° C. gave a red oil. Water was added to the crude product and the mixture was concentrated to dryness. This procedure was repeated several times until a clear, bright yellow homogenous aqueous solution was obtained. A few drops of 10% aqueous sodium thiosulfate was added to the yellow solution giving a clear, colorless solution. Lyophilization provided the title F product as an off-white solid (0.88 g). The crude product was further purified to 99+% HPLC purity by anion exchange chromatography (AG-1 X-2, formate form). Those fractions which contained the desired product (in >99% purity) were combined and concentrated to give 0.38 g (55%) of the title F product as a white solid. m.p.: >250° C.

Mass spectrum: (FAB) $1379.5^+$ $(M+H)^+$; $1321.5^+$ $(M+H-CH_2COOH)$. Microanalysis: Calculated for $C_{66}H_{98}N_{12}O_{20}\cdot 3.31\ H_2O$: C, 55.08; H, 7.33; N, 11.68; O, 25.91. Found: C, 55.18; H, 7.35; N, 11.58.

EXAMPLE 12A 10,10'-[[[[1,2-Ethanediyl]bis[(carboxymethyl)nitrilo]]bis(2-oxo-2,1-ethanediyl)bis[(4-cyclohexylphenyl)nitrilo]]bis(2-oxo-2,1-ethanediyl)bis[1,4,7,10-tetraazacyclododecane-1,4,7-triacetic acid]digadolinium disodium salt ("$Gd_2$-DAD-DO3A")

56 mg of the title compound of Example 12 were dissolved in 20 mL of distilled deionized water. 35 mg of $Gd_2O_3$ was added and the mixture was heated at 0° C. for 18 hours. The pH of the reaction mixture was adjusted to 7 with aqueous sodium hydroxide to precipitate gadolinium. The precipitate was removed by millipore filtration. The filtrate was concentrated to dryness. The solid material was purified by semipreparative HPLC. Product containing fractions were collected and concentrated by rotary evaporation. This gave the title product as a solid material (55 mg, 79% yield) which was dried at 80° C. in a vacuum oven.

Mass spectrum (FAB+): m/z at 1727 to 1737 $(M-H+2Na)^+$ and 1749 to 1759 $(M-2H+3Na)^+$. Microanalysis: Calculated for $C_{66}H_{90}N_{12}O_{20}Gd_2Na_2\cdot 22\ H_2O$: C,37.25; H, 6.23; N, 7.89. Found: C,37.29; H, 4.80; N, 7.80.

EXAMPLE 13

10-[2-N-(4-cyclohexylphenyl)-N-(carboxyethyl)amino]-2-oxoethyl]-1,4,7,10-tetraazacyclododecane-1,4,7-triacetic acid ("HCPA-DO3A")

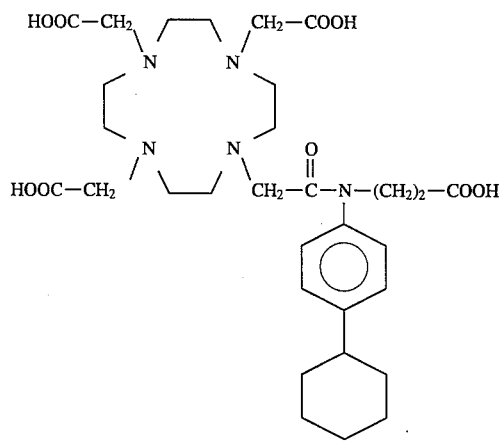

A. t-Butyl-N-(4-Cyclohexylphenyl)aminopropanoate

4-Cyclohexylaniline (70.1 g) was dissolved in 160 mL of tetrahydrofuran (THF) and stirred. Mercuric acetate (25.4 g) and t-butyl-acrylate (11.7 mL) were added sequentially and the mixture was stirred 7 hours at ambient temperature. 4-Cyclohexylaniline (14.02 g) was added to the solution followed by 0.5N aqueous sodium hydroxide solution (80 mL), and a solution of sodium borohydride (6.05 g) in 2.5N aqueous sodium hydroxide solution (32 mL). After 17.5 hours, the metallic mercury formed was collected. The resulting mixture was extracted with ether, the organic layers were pooled, washed with water and dried with sodium sulfate. The volatiles were removed and the resulting solid was purified by flash chromatography to afford 13.7 g (56.5 % yield) of the title A product as light yellow solid.

Microanalysis: Calc'd for $C_{19}H_{29}NO_2$: C, 75.21; H, 9.63; N, 4.62; O, 10.55. Found: C, 75.02; H, 9.37; N, 4.78

B. t-Butyl-[N-(4-cyclohexylphenyl)-N-(chloroacetyl)]aminopropanoate

A dry 500 mL round bottomed flask equipped with a magnetic stir bar and a septum-capped inlet was maintained under an atmosphere of dry nitrogen. The flask was charged with the title A compound (35 mmol) and N,N-dimethylacetamide (DMA) (60 mL). The mixture was stirred until the solid dissolved; then chloroacetyl chloride (5.14 g) was added at ambient temperature under nitrogen. The mixture was stirred for 2.5 hours and the volatiles were removed. The residue was dissolved in dichloromethane and was washed sequentially with saturated sodium bicarbonate solution, water and saturated sodium chloride solution (2×60 mL). The organic layer was dried with $Na_2SO_4$. This afforded 12.6 g (95% yield) of the crude product as a pink solid which was recrystallized in hexanes/ethyl acetate to give 8.1 g (61%) of pure title B product of >98% purity (HPLC). m.p.: 87.3°–88.1° C.

Microanalysis: Calc'd for $C_{21}H_{30}NO_3Cl$: C, 66.39; H, 7.96; N, 3.69; Cl, 9.33; O, 12.63. Found:C, 66.31; H, 7.85; N, 4.02; Cl, 9.33; O, NA.

C. 10-[2-(N-4-Cyclohexylphenyl)-N-tert-butoxycarbonylethyl)amino]-2-oxoethyl-1,4,7-tris(tert-butoxycarbonylmethyl)-1,4,7,10-tetraazacyclododecane A flask containing 1,4,7-tris(tert-butoxycarbonylmethyl)-1,4,7,10-tetraazacyclododecane free base (see Example 3) (10.2 g) was charged with acetonitrile (HPLC grade, 65 mL), powdered anhydrous potassium carbonate (6.21 g), title B compound (6.82 g) and NaI (2.70 g) in that order. The mixture was stirred at 50°–60° C. for 50 hours under nitrogen. Then the mixture was diluted with acetonitrile (600 mL) and the salts were removed by rotary evaporation. The resulting solid was pumped overnight at high vacuum to provide the title C product as pale yellow foam (16.8 g, excess of theoretical).

Mass Spectrum: 880 (M+Na)$^+$, 824 (M+Na—C$_4$H$_8$)$^+$, 780 (M$^+$-COO(CH$_3$)$_3$).

D. 10-[2-(N-4-Cyclohexylphenyl)-N-carboxyethyl)amino]-2-oxoethyl-1,4,7,10-tetraazacyclododecane-1,4,7-triacetic acid A 1000 mL oven-dried flask equipped with a magnetic stir bar and a septum capped inlet was maintained under nitrogen. The flask was charged with the title C compound (16.8 g) and a mixture of anisole (59 mL) and trifluoroacetic acid (589 mL). The mixture was stirred for 5 hours at ambient temperature under nitrogen. The volatiles were removed and the mixture was pumped overnight under high vacuum. This gave 11.5 g (100% yield) of the crude product as a brown glass.

The crude product was dissolved in distilled, deionized water (200 mL) and the water was removed by rotary evaporation using a water aspirator pump. This procedure was repeated 4 times. Distilled deionized water (125 mL) was added to the resulting solid, and the pH of the solution was adjusted to about 6 by addition of dilute sodium hydroxide solution. The resulting material was purified by ion exchange chromatography to afford 7.9 g (69.3% yield) of the desired title D product as a white glass.

Microanalysis: Calc'd for C$_{31}$H$_{47}$N$_5$O$_9$: C, 56.11; H, 7.64; N, 10.55; O, 25.69. Found for C$_{31}$H$_{47}$N$_5$O$_9$: C, 56.43; H, 7.78; N, 10.55.

EXAMPLE 13A

10-[2-[N-(4-Cyclohexylphenyl)-N-(carboxyethyl) amino]-2-oxoethyl]-1,4,7,10-tetraazacyclododecanato-1,4,7-triacetic acid gadolinium ("Gd-HCPA-DO3A")

The title product of Example 13 (free acid form) (1.4 g) was dissolved in 50 mL distilled-deionized water. Then gadolinium triacetate (Gd(OAc)$_3$·4H$_2$O) (1.08 g) was added. The mixture was stirred at 80° C. for 1 hour and then at room temperature for 4.5 hours. Excess gadolinium was removed by precipitation as its hydroxide, and the pH of the solution was then adjusted to 6.5 with 0.02M hydrochloric acid solution. The resulting material was purified by reverse phase preparative column chromatography using a water-ethanol gradient elution to afford 1.6 g (92% yield) of the title product as a white lyophilizate.

Mass Spectrum: 789 (M+H)$^+$, 811 (M+Na)$^+$, 833 (M+2Na—H)$^+$.

Microanalysis: Calc for C$_{31}$H$_{43}$N$_5$O$_9$NaGd.3.03H$_2$O C, 43.07; H, 5.72; N, 8.10; Na, 2.66; Gd, 18.19; O, 22.26 Found: C, 43.33; H, 5.92; N, 7.96.

EXAMPLE 14

10-[2-[[2-[(Carboxymethyl)[2-[[[(4-cyclohexylphenyl)-[(4,7,10-tris(carboxymethyl)-1,4,7,10-tetraazacyclododec-1-yl]acetyl]amino]acetyl]amino] ethyl]amino]-2-oxoethyl](4-cyclohexylphenyl)amino]-2-oxoethyl]-1,4,7,10-tetraazacyclododecane-1,4,7-triacetic acid ("MAD-DO3A")

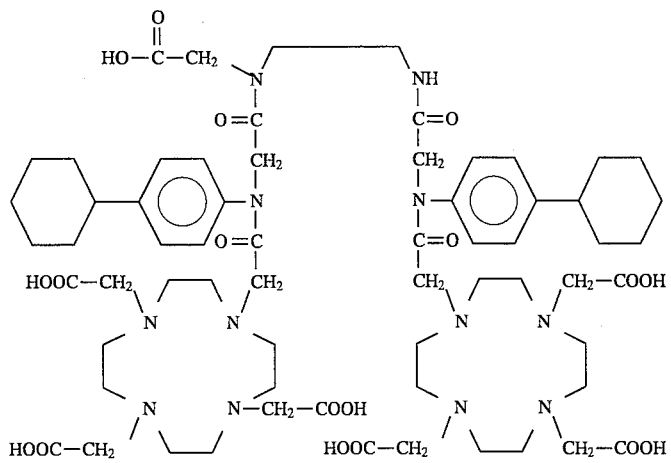

A. [(2-Aminoethyl)amino]acetic acid, 1,1-dimethylethyl ester

The title A compound was synthesized according to a modification of the procedure of Cuenoud et al., *Tetrahedron*, 47, 2535–2542 (1991). Ethylenediamine (4.4 g) was placed into a dry 100 mL round bottom flask equipped with a stir bar and cooled to 5° C. with ice. tert-Butylbromoacetate (0.75 g) was added dropwise over a 1 hour period. Upon complete addition, the reaction was allowed to stir at 0°–5° C. for 1 hour and then at room temperature for an additional 1 hour. Solvent removal in vacuo at 35° C. gave a pale yellow oil which was diluted with chloroform (175 mL) and allowed to stir at room temperature for 0.5 hour. The insoluble ethylenediamine dihydrobromide was removed by filtration and washed several times with chloroform. The mother liquor and washings were concentrated at room temperature to a viscous yellow oil (0.53 g, 79% yield). Analysis by $^1$H-NMR indicated that the crude title A ester was sufficiently pure to use directly in the next step. TLC: R$_f$=0.50 (silica gel, ammonia saturated methanol, ninhydrin detection)

Mass spectrum: (CI) m/e 174 (M+H)$^+$, 119 (M+H-isobutylene).

B. [(Chloroacetyl)[2-[(chloroacetyl)amino]ethyl]amino] acetic acid, 1,1-dimethylethyl ester Chloroacetyl chloride (2.9 g) in anhydrous CHCl$_3$ (10 mL) and potassium carbonate (2.60 g) in water (10 mL)

were simultaneously added through separate addition funnels to a stirred solution of the title A aminoester (1.5 g, 8.6 mmol) in CHCl$_3$ (20 mL) at 0°–5° C. over a 1 hour period. The mixture was stirred an additional 2 hours at 25° C. The chloroform layer was separated and washed twice with water (10 mL). The organic layer was dried over anhydrous magnesium sulfate and the solvent was removed in vacuo to give a crude product which was chromatographed on silica gel (eluted with gradient from 45% ethyl acetate in hexanes to 80% ethyl acetate in hexanes) to obtain the title B bischloroamide as a clear colorless oil (2.4 g, 86% yield).

Microanalysis: Calculated for $C_{12}H_{20}N_2Cl_2O_4 \cdot 0.26 H_2O$: C, 43.43; H, 6.23; N, 8.44; Cl, 21.37; O, 20.53%. Found: C, 43.64; H, 6.07; N, 8.23; Cl, 21.05%.

C. [[[(4-Cyclohexylphenyl)amino]acetyl][2-[[[(4-cyclohexylphenyl)amino]acetyl]amino]ethyl]amino]acetic acid, 1,1-dimethylethyl ester Cyclohexylaniline (9.5 g), potassium carbonate (10.6 g) and sodium iodide (8.1 g) were mixed together in anhydrous acetonitrile (100 mL). To this stirred solution at ambient temperature was added the title B bis-chloroamide (8.42 g, 25.8 mmol) dissolved in acetonitrile (40 mL) dropwise over a one-hour period. Stirring was continued for an additional 18 hours at ambient temperature. The precipitate which formed was removed by filtration, washed with two portions of cold acetonitrile (100 mL), and dried in vacuo to a yellow solid. The solid residue was redissolved in CH$_2$Cl$_2$ (1.5 l) and washed with water (3×250 mL), 1% sodium thiosulfate (1×200 mL) and saturated sodium chloride (1×250 mL). The organic layer was dried over magnesium sulfate, filtered and concentrated to a pale yellow solid. This material was re-suspended in acetonitrile (100 mL), filtered and re-washed with cold acetonitrile (2×30 mL) to give a white solid (8.2 g, 53%) which was a single spot by TLC. The title C material obtained was used directly for the next step without further purification.

Microanalysis: Calculated for $C_{36}H_{52}N_4O_4 \cdot 0.14 H_2O$: C, 71.19; H, 8.68; N, 9.22; O, 10.91%. Found: C, 70.85; H, 8.55; N, 9.04; H$_2$O, 0.42%.

D. [[[(Chloroacetyl)(4-cyclohexylphenyl)amino]acetyl][2-[[[(chloroacetyl)(4-cyclohexylphenyl)amino]acetyl]amino]ethyl]amino]acetic acid. 1,1-dimethylethyl ester The title C bisamide (0.97 g) was dissolved in anhydrous dimethylacetamide (DMA) (60 mL) and cooled to 5° C. To this cooled solution was added chloroacetyl chloride (0.45 mL) dropwise over a 0.5 hour period. Stirring was continued at 5° C. for 2 hours and then at room temperature for 1 hour. The solution was concentrated in vacuo at 40° C. to give a yellow oil. The residue was dissolved in CH$_2$Cl$_2$ (200 mL) and washed with water (2×75 mL), saturated sodium bicarbonate (75 mL) and saturated aqueous sodium chloride (75 mL). The organic layer was dried (MgSO$_4$), filtered and concentrated to a yellow foam (1.25 g, 100%). The crude bis-chloro compound was further purified by silica gel chromatography to give pure title D compound (0.95 g, 76%) as a white solid. m.p.: 112°–115° C.

Microanalysis: Calculated for $C_{40}H_{54}N_4Cl_2O_6 \cdot 27 H_2O$. C, 63.00; H, 7.21; N, 7.35; Cl, 9.30; O, 13.15%. Found: C, 62.56; H, 7.00; N, 7.36; Cl, 9.08; H$_2$O, 0.63%.

E. 10-[2-[(4-Cyclohexylphenyl)[2-[[2-[[[(4-cyclohexylphenyl)][4,7,10-tris[2-(1,1-dimethylethoxy)-2-oxoethyl]-1,4,7,10-tetraazacyclododec-1-yl]acetyl]amino]acetyl]amino]ethyl][2-(1,1-dimethylethoxy)-2-oxoethyl]amino]2-oxoethyl]amino]-2-oxoethyl]-1,4,7,10-tetraazacyclododecane-1,4,7-triacetic acid, tris (1,1-dimethylethyl)ester 1,4,7,10-Tetraazacyclododecane-1,4,7-triacetic acid, tris(1,1-dimethylethyl)ester, monohydrochloride (prepared in Example 3C) (15.5 g) and potassium carbonate (6.10 g) were mixed together in anhydrous dimethylformamide (DMF) (100 mL) and stirred at room temperature for 0.5 hour. To this solution was added sodium iodide (3.94 g). To this heterogenous solution, heated to 55° C., was added the title D bischlorotetraamide in DMF (30 mL) dropwise over a 1 hour period. The mixture was stirred at 55° C. for 40 hours. The mixture was concentrated in vacuo to remove DMF and the residue was dissolved in CH$_2$Cl$_2$ (500 mL). The solution was washed with water (2×175 mL) and saturated aqueous sodium chloride (100 mL). The organic layer was dried (sodium sulfate), filtered and concentrated in vacuo to a yellow foam (29 g, 135%) of the title E compound. The product was used directly in the next step without further purification.

Mass spectrum: (FAB) m/e 1715.2 (M+H), 1736.2 (M+Na), 1886 (M+2Na+I).

F. 10-[2-[[2-[(Carboxymethyl)[2-[[[(4-cyclohexylphenyl)-[(4,7,10-tris(carboxymethyl)-1,4,7,10-tetraazacyclododec-1-yl]acetyl]amino]acetyl]amino]ethyl]amino]-2-oxoethyl](4-cyclohexylphenyl)amino]-2-oxoethyl]-1,4,7,10-tetraazacyclododecane-1,4,7-triacetic acid, tris triethylamine salt The crude title E compound (27 g) was treated with trifluoroacetic acid (300 mL) and anisole (30 mL) with stirring at room temperature overnight. Upon completion of the reaction, the dark red solution was concentrated in vacuo at 45° C. The remaining residue was mixed with water and concentrated in vacuo. This was repeated several times until the aqueous solution was a clear homogeneous dark-yellow solution free of anisole. Aqueous 1% sodium thiosulfate solution was added to the aqueous solution containing the crude title F compound; this removed the dark yellow color. Ion exchange chromatography (AG50W-X$_2$ and DEAE Sephadex A-25) provided 3.5 g of the pure title F tristriethylamine salt.

Microanalysis: Calculated for $C_{64}H_{96}N_{12}O_{18} \cdot 2.5 H_2O \cdot 3(CH_3CH_2)_3N$: C, 58.97; H, 8.81; N, 12.48; O, 19.74%. Found: C, 59.31; H, 8.60; N, 12.08; H$_2$O, 2.70%.

G. 10-[2-[[2-[(Carboxymethyl)[2-[[[(4-cyclohexylphenyl)-[(4,7,10-tris(carboxymethyl)-1,4,7,10-tetraazacyclododec-1-yl]acetyl]amino]acetyl]amino]ethyl]amino]-2-oxoethyl](4-cyclohexylphenyl)amino]-2-oxoethyl]-1,4,7,10-tetraazacyclododecane-1,4,7-triacetic acid 1.1 g of the title F salt was converted to the corresponding free acid by passage through a Bio-Rad AG1-X2 anion exchange resin (formate form) column eluting with water, followed by 1M formic acid. Combination of those fractions containing the desired ligand yielded 623 mg of the title G compound as the free acid. m.p.: 240°–246° C. (dec.)

Microanalysis: Calculated for $C_{64}H_{96}N_{12}O_{18} \cdot 2.55H_2O$: C, 56.21; H, 7.45; N, 12.29; O, 24.04%. Found: C, 56.15; H, 7.65; N, 12.19; H$_2$O, 3.36%.

EXAMPLE 14A

10-[2-[[2-[(Carboxymethyl)[2-[[[(4-cyclohexylphenyl)-[(4,7,10-tris(carboxymethyl)-1,4,7,10-tetraazacyclododec-1-yl]acetyl]amino]acetyl]amino]ethyl]amino]-2-oxoethyl](4-cyclohexylphenyl)amino]-2-oxoethyl]-1,4,7,10-tetraazacyclododecane-1,4,7-triacetic acid, digadolinium disodium salt ("Gd-MAD-DO3A")

The title chelate was prepared from the reaction of the acid form of the title compound of Example 14 (66 mg) and GdCl$_3$ (11.0 mL of 9.17 mM solution). The crude material was purified by semi-prep HPLC. Product containing fractions were collected and concentrated to dryness by heating at 60° C. under the stream of nitrogen. The solid sample was dried under vacuum at 70° C. This gave 35 mg (55% yield) of the title product as a solid.

Mass spectrum (FAB+): m/Z: 1653 $(M+Na+H^+)^+$. Microanalysis: Calc'd for $NaC_{64}H_{90}N_{12}O_{18}Gd_2$ 7.0 $H_2O$: C,43.21; H, 5.89; N, 9.44. Found: C, 43.53; H, 6.38; N, 9.52.

EXAMPLE 15

10-[2-[(2-Sulfonyloxyethyl)[4-cyclohexylphenyl] amino]-2-oxoethyl]-1,4,7,10-tetraazacyclododecane-1,4,7-triacetic acid ("SCPA-DO3A")

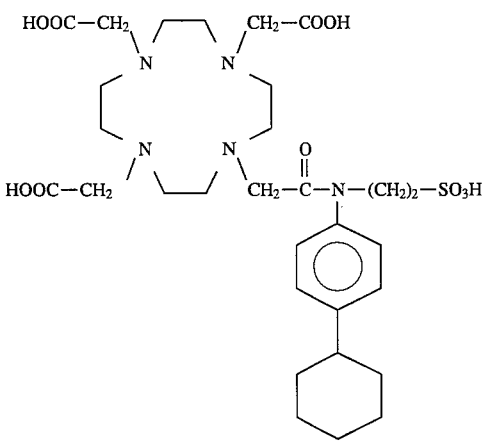

A. 4-(Cyclohexylphenyl)aminoethane sulfonic acid

A dry 250 mL round bottomed flask was charged with 4-cyclohexylaniline (47.32 g) and sodium 2-bromoethanesulfonate (18.99 g) and then heated to 175° C. with stirring. The mixture was stirred for 8 hours and then the flask was removed from the bath and allowed to cool to ambient temperature. Excess 4-cyclohexylaniline was removed by addition of aqueous sodium hydroxide to the solid mass and partitioning the mixture between the aqueous layer and ethyl ether. The mixture was shaken vigorously for 30 min. and the suspension of the pale tan sodium salt was filtered through Whatman #50 filter paper; the solid collected was washed several times with ether.

The collected solid (from the filtration) was added to 150 mL of distilled deionized water and 10 mL of concentrated HCl. The volatiles were removed and a 22.5 g portion of the yellow solid collected by filtration was added to 60 mL of distilled, deionized water. A solution of 1.25M NaOH (80 mL) was added. This resulting mixture was stirred and the volume was adjusted to 200 mL with distilled, deionized water. The resulting suspension of the sodium salt was filtered and the wet cake was well agitated with ether twice. The sodium salt of the title A product was dried over phosphorus pentoxide to give 17.76 g of a tan solid. A 16.4 g portion was neutralized with 230 mL of 0.5M HCl to provide, after drying, 14.26 g (55.9%) of the desired title A product as a yellow solid.

Microanalysis: Calc'd for $C_{14}H_{21}NO_3Cl \cdot 0.06\ H_2O \cdot 0.04$ p-cyclohexylaniline hydrochloride: C, 59.38; H, 7.52; N, 4.98; Cl, 0.51. Found: C, 59.41; H, 7.55; N, 4.90; Cl; 0.93.

B. N-(Chloroacetyl),4-(cyclohexylphenyl)aminoethane sulfonic acid

A 250 mL round bottomed flask equipped with magnetic stir bar and septum capped inlet was charged with the title A compound (8.60 g), chloroacetyl chloride (10 g) and N,N-dimethylacetamide ("DMA") (80 mL). The mixture was stirred at 0° C. for 5 min. and then for 24 hours at ambient temperature. The volatiles were removed by rotary evaporation at high vacuum. Then deionized water (150 mL) was added and the mixture was filtered. The resulting solution was lyophilized to give a brown oil which was triturated with ethyl acetate to give a solid material. The volatiles were removed at high vacuum and the solid was recrystallized from ethyl acetate. This gave a first crop of 5.53 g (41.2% yield). A second crop of crystals provided 3.33 g (24.8% yield) of the product. The two crops were pumped on for 3 days to remove residual HCl from the product as its 1:1 DMA complex. The title B product was obtained as a 1:1 DMA adduct.

Microanalysis: Calc'd for 1:1 title B compound:DMA adduct: C, 53.76; H, 6.99; N, 6.27; S, 7.17; Cl, 7.93. Found: C, 53.76; H, 7.07; N, 6.24; S, 6.93; Cl, 7.92.

C. 10-[2-[(2-Sulfonyloxyethyl)[4-cyclohexylphenyl]-amino]-2-oxoethyl]-1,4,7,10-tetraazacyclododecane-1,4,7-triacetic acid, tris-tert-butyl ester A dry 250 mL recovery flask equipped with a magnetic stir bar and septum-capped inlet was charged with 1,4,7,10-tetraazacyclododecane, 1,4,7-tris(1,1-dimethylethyl)ester (see Example 3) (9.86 g), acetonitrile (40 mL), potassium carbonate (7.96 g), Hünigs base (N,N-diisopropylethylamine) (2.58 g), the title B compound (8.57 g), sodium iodide (2.44 g) and distilled deionized water (0.5 g). The mixture was stirred and solidified within 2 min. N,N-dimethylacetamide (35 mL) was therefore added and the mixture was stirred at 68°–70° C. for 72 hours. The reaction was complete as judged by the disappearance of the starting tetraazacyclododecane. The salts were filtered and the volatiles were removed by rotary evaporation to provide 22.20 g (132% of theoretical) of the crude title C alkylate as a reddish foam. HPLC: Ret time: 7.76 min. System: Shimadzu $LC_6A$ with CR6A integrator. Column: PLRP-S reverse phase 250 mm×4.6 mm i.d.; Eluent: 60% $CH_3CN$ in 0.05M $NaH_2PO_4$ pH=4.5; Flow rate: 1.0 mL/min.; Detection: UV@254 nm.

D. 10-[2-[(2-Sulfonyloxyethyl)[4-cyclohexylphenyl]amino]-2-oxoethyl]-1,4,7,10-tetraazacyclododecane-1,4,7-triacetic acid The crude title C alkylate (21.2 g) was added to a dry 1000 mL round bottomed flask equipped with a magnetic stir bar and a septum capped inlet and was treated with a mixture of anhydrous trifluoroacetic acid (550 mL) and anisole (70 mL) for 4.75 hours. The volatiles were removed. Traces of anisole and iodine were removed by coevaporation with water. The resulting residue was pumped on at high vacuum overnight to provide the crude product as an orange yellow foam. This was purified by ion exchange column chromatography to provide the desired title D product, 9.35 g (81%.yield from the title C compound) as a white lyophilizate.

Microanalysis: Calc'd for $C_{30}H_{47}N_5SO_{10} \cdot 1.64\ H_2O$: C, 51.53; H, 7.25; N, 10.01; S, 4.58 Found: C, 52.12; H, 7.38; N, 10.01; S, 4.67. (These values are consistent with 1.49 moles of water, within the error of the KF determination.)

EXAMPLE 15A

10-[2-[N-(2-Sulfonyloxyethyl)-(4-cyclohexylphenyl) amino]-2-oxoethyl]-1,4,7,10-tetraazacyclododecanatogadolinium monosodium salt ("Gd-SCPA-DO3A")

The title compound of Example 15 (4.0 g) was dissolved in 140 mL distilled-deionized water. Then $Gd(OAc)_3 \cdot 4H_2O$ (2.91 g) was added. The mixture was stirred at 60° C. for 6 hours and then cooled to ambient temperature. Excess gadolinium was removed by precipitation with aqueous sodium hydroxide, and filtration. The pH of the solution was then adjusted to 6.5 with a dilute hydrochloric acid solution. The chelate was purified by reverse phase preparative column chromatography to afford 4.97 g (98% yield) of the desired title product as a white lyophilizate.

Microanalysis: Calc for $C_{30}H_{44}N_5O_{10}SNaGd \cdot 5.24H_2O$ C, 38.28; H, 5.83; N, 7.44; S, 3.41; Na, 2.44; Gd, 16.71; O, 25.90. Found: C, 38.36; H, 5.72; N, 7.48; S, 3.22.

What is claimed is:

1. A compound of the following formula I:

$$Q-(CH_2)_m-\overset{O}{\underset{\|}{C}}-\overset{R}{\underset{|}{N}}-A_1-\underset{R_2}{\overset{R_1}{\text{C}_6H_3}} \qquad I$$

wherein

Q is a polyaza macrocyclic group containing at least one aminocarboxylate, aminophosphonate and/or aminohydroxamate chelating group;

$A_1$ is $(CH_2)_{m'}$, $(CH_2)_n-O-(CH_2)_{n'}$ or a single bond;

$(CH_2)_m$ and $(CH_2)_{m'}$ may be independently substituted with alkyl or hydroxyalkyl;

R is $$\underset{(CH)_n-COX,}{\overset{R_{11}}{|}} \quad \underset{(CH)_n-SO_3H}{\overset{R_{11}}{|}}$$

or $-[(CH_2)_2-Y]-R_{13}$;

X is $-OH$, $-O$-alkyl or $-NHR_{12}$;

Y is $-O-$ or $-NH-$;

$R_1$ and $R_2$ are each independently hydrogen, alkyl, cycloalkyl, aryl, arylalkyl, $-NO_2$, $-NH_2$, $$\underset{-NHCNHR_{12},}{\overset{S}{\underset{\|}{}}} \quad -NCS, \quad \underset{-C-NR_3R_4,}{\overset{O}{\underset{\|}{}}}$$

$-COOH$, $-N-N^+\equiv N^-$, $-NR_3COR_9$, haloalkyl, $C_{1-8}$ alkoxy, aryloxy, cycloalkyloxy, or a functional group capable of forming a conjugate with a biomolecule or of forming a multimer of said compound of the formula I, or $R_1$ and $R_2$ together with the phenyl ring to which they are bonded form a naphthyl group, with the proviso that at least one of $R_1$ or $R_2$ must be other than hydrogen;

$R_3$ and $R_4$ are independently hydrogen, alkyl, arylalkyl, aryl, alkoxy or hydroxyalkyl, or $R_3$ and $R_4$, together with the nitrogen atom to which they are bonded, form a maleimide group;

$R_9$ is alkyl or hydroxyalkyl;

each $R_{11}$ is independently hydrogen or alkyl;

$R_{13}$ is $-CH_2COOH$ or $-CH_2CONHR_{12}$;

$R_{12}$ is hydrogen, alkyl, $-NH_2$, $$\underset{-(CH)_{n'''}-SO_3H,}{\overset{R_{11}}{|}} \quad \underset{-(CH)_{n'''}-CO-O-alkyl,}{\overset{R_{11}}{|}}$$

$$\underset{-(CH)_{n'''}-COOH}{\overset{R_{11}}{|}}$$

or hydroxyalkyl;

n, m', n, n' and n''' are independently 1 to 5;

or a salt and/or a multimeric form thereof.

2. A compound of claim 1, wherein said compound has the following formula I', I'', I''' or I'''', or a salt and/or multimer thereof:

[Structure I' showing a tetraazacyclododecane macrocycle with four nitrogen atoms, three bearing $X_1-HC(R_{14})-$ groups and one bearing $-(CH_2)_m-C(=O)-N(R)-A_1-$ phenyl with $R_1, R_2$ substituents]

wherein m, R, $A_1$, $R_1$ and $R_2$ are as defined above and further wherein $X_1$ is $-COOY_1$, $-PO_3HY_1$ or $-CONHOY_1$, where $Y_1$ is a hydrogen atom, or a cation;

$R_{14}$ is hydrogen, alkyl, hydroxyalkyl or aralkyl.

3. A compound of claim 1 which is selected from the group consisting of:

10-[2-[(carboxymethyl)-(4-methylphenyl)amino]-2-oxoethyl]-1,4,7,10-tetraazacyclododecane-1,4,7-triacetic acid;

10-[2-[(carboxymethyl)]-4-(1,1-dimethylethyl)phenyl]-amino]-2-oxoethyl]-1,4,7,10-tetraazacyclododecane-1,4,7-triacetic acid;

10-[2-[([1,1'-biphenyl]-4-yl)(carboxymethyl)amino]-2-oxoethyl]-1,4,7,10-tetraazacyclododecane-1,4,7-triacetic acid;

10-[2-[(2-carboxymethyl)[2,5-di-tert-butylphenyl)amino]-2-oxoethyl]-1,4,7,10-tetraazacyclododecane-1,4,7-triacetic acid;

10-[2-[(carboxymethyl)(3,5-di-(1,1-dimethylethyl)-phenyl)amino]-2-oxoethyl]-1,4,7,10-tetraazacyclododecane-1,4,7-triacetic acid;

10-[2-[(carboxymethyl)[4-(cyclohexyl)phenyl]amino]-2-oxoethyl]-1,4,7,10-tetraazacyclododecane-1,4,7-triacetic acid;

10-[2-[(carboxymethyl)(4-n-decylphenyl)amino]-2-oxoethyl]-1,4,7,10-tetraazacyclododecane-1,4,7-triacetic acid;

10-[2-[[3,5-bis[[(2-methylbutyl)amino]carbonyl]phenyl]-(carboxymethyl)amino]-2-oxoethyl]-1,4,7,10-tetraazacyclododecane-1,4,7-triacetic acid, triethylamine (1:2) salt;

10-[2-[N-(4-cyclohexylphenyl)-N-(2-amino-2-oxoethyl)-amino]-2-oxoethyl]-1,4,7,10-tetraazacyclododecane-1,4,7-triacetic acid;

10-[2-[N-(4-cyclohexylphenyl)-N-[2-(N-carboxymethyl)aminoethyl]amino]-2-oxoethyl]-1,4,7,10-tetraazacyclododecane-1,4,7-triacetic acid;

10,10'-[[[[1,2-ethanediylbis[(carboxymethyl)nitrilo]]-bis(2-oxo-2,1-ethanediyl)bis[(4-cyclohexyl)phenyl)nitrilo]]bis(2-oxo-2,1-ethanediyl)bis[1,4,7,10-tetraazacyclododecane-1,4,7-triacetic acid];

10-[2-N-(4-cyclohexylphenyl)-N-(carboxyethyl)amino]-2-oxoethyl]-1,4,7,10-tetraazacyclododecane-1,4,7-triacetic acid;

10-[2-[[2-[(carboxymethyl)[2-[[[(4-cyclohexylphenyl)-[(4,7,10-tris(carboxymethyl)-1,4,7,10-tetraazacyclododec-1-yl]acetyl]amino]acetyl]amino]ethyl] amino]-2-oxoethyl](4-cyclohexylphenyl)amino]-2- oxoethyl]-1,4,7,10-tetraazacyclododecane-1,4,7-triacetic acid;

10-[2-[(2-sulfonyloxyethyl)[4-cyclohexylphenyl]-amino]-2-oxoethyl]-1,4,7,10-tetraazacyclododecane-1,4,7-triacetic acid;

and salts thereof.

4. A metal chelate, comprising a compound of claim 1 complexed with a metal atom.

5. The chelate of claim 4, wherein said metal is selected from atoms having an atomic number of 21 to 29, 39 to 50, or 57 to 83.

6. The chelate of claim 5, wherein said metal is gadolinium.

7. The chelate of claim 6, wherein said compound of claim 1 is selected from the group consisting of:

10-[2-[(carboxymethyl)-(4-methylphenyl)amino]-2-oxoethyl]-1,4,7,10-tetraazacyclododecane-1,4,7-triacetic acid;

10-[2-[(carboxymethyl)]-4-(1,1-dimethylethyl)phenyl]-amino]-2-oxoethyl]-1,4,7,10-tetraazacyclododecane-1,4,7-triacetic acid;

10-[2-[([1,1'-biphenyl]-4-yl)(carboxymethyl)amino]-2-oxoethyl]-1,4,7,10-tetraazacyclododecane-1,4,7-triacetic acid;

10-[2-[(2-carboxymethyl)[2,5-di-tert-butylphenyl)amino]-2-oxoethyl]-1,4,7,10-tetraazacyclododecane-1,4,7-triacetic acid;

10-[2-[(carboxymethyl)(3,5-di-(1,1-dimethylethyl)-phenyl)amino]-2-oxoethyl]-1,4,7,10-tetraazacyclododecane-1,4,7-triacetic acid;

10-[2-[(carboxymethyl)[4-(cyclohexyl)phenyl]amino]-2-oxoethyl]-1,4,7,10-tetraazacyclododecane-1,4,7-triacetic acid;

10-[2-[(carboxymethyl)(4-n-decylphenyl)amino]-2-oxoethyl]-1,4,7,10-tetraazacyclododecane-1,4,7-triacetic acid;

10-[2-[[3,5-bis[[(2-methylbutyl)amino]carbonyl]phenyl]-(carboxymethyl)amino]-2-oxoethyl]-1,4,7,10-tetraazacyclododecane-1,4,7-triacetic acid, triethylamine (1:2) salt;

10-[2-[N-(4-cyclohexylphenyl)-N-(2-amino-2-oxoethyl)-amino]-2-oxoethyl]-1,4,7,10-tetraazacyclododecane-1,4,7-triacetic acid;

10-[2-[N-(4-cyclohexylphenyl)-N-[2-(N-carboxymethyl)aminoethyl]amino]-2-oxoethyl]-1,4,7,10-tetraazacyclododecane-1,4,7-triacetic acid;

10,10'-[[[[1,2-ethanediylbis[(carboxymethyl)nitrilo]]-bis(2-oxo-2,1-ethanediyl)bis[(4-cyclohexyl]phenyl)nitrilo]]bis(2-oxo-2,1-ethanediyl)bis[1,4,7,10-tetraazacyclododecane-1,4,7-triacetic acid];

10-[2-N-(4-cyclohexylphenyl)-N-(carboxyethyl)amino]-2-oxoethyl]-1,4,7,10-tetraazacyclododecane-1,4,7-triacetic acid;

10-[2-[[2-[(carboxymethyl)(2-[[[(4-cyclohexylphenyl)-[(4,7,10-tris(carboxymethyl)-1,4,7,10-tetraazacyclododec-1-yl]acetyl]amino]acetyl]amino]ethyl]amino]-2-oxoethyl](4-cyclohexylphenyl)amino]-2-oxoethyl]-1,4,7,10-tetraazacyclododecane-1,4,7-triacetic acid;

10-[2-[(2-sulfonyloxyethyl)[4-cyclohexylphenyl]-amino]-2-oxoethyl]-1,4,7,10-tetraazacyclododecane-1,4,7-triacetic acid;

10-[2-[N-(4-cyclohexylphenyl)-N-[(2-sulfonyloxyethyl)amino-2-oxoethyl]amino]-2-oxoethyl]-1,4,7,10-tetraazacyclododecane-1,4,7-triacetic acid;

and salts thereof.

8. The chelate of claim 7, wherein said chelate is the Major conformer and/or the Minor conformer of the chelate wherein said compound of claim 1 is 10-[2-[(2-carboxymethyl)[2,5-di-tert-butylphenyl)-amino]-2-oxoethyl]-1,4,7,10-tetraazacyclododecane-1,4,7-triacetic acid.

9. A pharmaceutical composition, comprising a compound of claim 1, optionally complexed with a metal, and a pharmaceutically acceptable vehicle or diluent.

10. A method for diagnostic imaging, comprising the steps of administering to a host a compound of claim 1, which compound is complexed with a metal, and obtaining a diagnostic image of said host.

11. The method of claim 10, wherein said image is a magnetic resonance image.

12. The method of claim 11, wherein said metal is gadolinium, and said image comprises an image of the hepatobiliary system of said host.

13. A conjugate, comprising a compound of claim 1 conjugated with a biomolecule.

14. A metal chelate, comprising a conjugate of claim 13, wherein said compound of claim 1 is complexed with a metal atom.

15. A pharmaceutical composition, comprising a conjugate of claim 13, optionally complexed with a metal, and a pharmaceutically acceptable vehicle or diluent.

16. A method for diagnostic imaging, comprising the steps of administering to a host a conjugate of claim 13, which conjugate is complexed with a metal, and obtaining a diagnostic image of said host.

* * * * *